US010344075B2

(12) United States Patent
Smith et al.

(10) Patent No.: US 10,344,075 B2
(45) Date of Patent: Jul. 9, 2019

(54) ENGINEERED HIGH-AFFINITY HUMAN T CELL RECEPTORS

(71) Applicants: The Board of Trustees of the University of Illinois, Urbana, IL (US); Fred Hutchinson Cancer Research Center, Seattle, WA (US)

(72) Inventors: Sheena N. Smith, Urbana, IL (US); Daniel T. Harris, Urbana, IL (US); David M. Kranz, Urbana, IL (US); Philip D. Greenberg, Seattle, WA (US); Thomas M. Schmitt, Seattle, WA (US)

(73) Assignees: THE BOARD OF TRUSTEES OF THE UNIVERSITY OF ILLINOIS, Urbana, IL (US); FRED HUTCHINSON CANCER RESEARCH CENTER, Seattle, WA (US)

( * ) Notice: Subject to any disclaimer, the term of this patent is extended or adjusted under 35 U.S.C. 154(b) by 0 days.

(21) Appl. No.: 15/037,485

(22) PCT Filed: Nov. 21, 2014

(86) PCT No.: PCT/US2014/066903
§ 371 (c)(1),
(2) Date: May 18, 2016

(87) PCT Pub. No.: WO2015/077615
PCT Pub. Date: May 28, 2015

(65) Prior Publication Data
US 2016/0280756 A1 Sep. 29, 2016

Related U.S. Application Data

(60) Provisional application No. 61/907,887, filed on Nov. 22, 2013.

(51) Int. Cl.
*A61K 38/00* (2006.01)
*C07K 14/735* (2006.01)
*C07K 14/725* (2006.01)
*C07K 14/47* (2006.01)

(52) U.S. Cl.
CPC ...... *C07K 14/7051* (2013.01); *C07K 14/4747* (2013.01); *A61K 38/00* (2013.01); *C07K 2317/565* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 6,300,065 | B1 | 10/2001 | Kieke et al. |
| 6,423,538 | B1 | 7/2002 | Wittrup et al. |
| 6,534,633 | B1 | 3/2003 | Weidanz et al. |
| 6,696,251 | B1 | 2/2004 | Wittrup et al. |
| 6,699,658 | B1 | 3/2004 | Wittrup et al. |
| 6,759,243 | B2 | 7/2004 | Kranz et al. |
| 7,465,787 | B2 | 12/2008 | Wittrup et al. |
| 7,569,357 | B2 | 8/2009 | Kranz et al. |
| 7,569,664 | B2 | 8/2009 | Jakobsen et al. |
| 7,608,410 | B2 | 10/2009 | Dunn et al. |
| 7,666,604 | B2 | 2/2010 | Jakobsen et al. |
| 7,763,718 | B2 | 7/2010 | Jakobsen et al. |
| 8,017,730 | B2 | 9/2011 | Jakobsen et al. |
| 8,088,379 | B2 | 1/2012 | Robbins et al. |
| 8,105,830 | B2 | 1/2012 | Weidanz et al. |
| 8,143,376 | B2 | 3/2012 | Boulter et al. |
| 10,023,625 | B2 | 7/2018 | Smith et al. |
| 2007/0191496 | A1* | 8/2007 | Stauss ............ C07K 14/7051 424/192.1 |
| 2008/0125369 | A1 | 5/2008 | Jakobsen et al. |
| 2010/0009863 | A1 | 1/2010 | Himmler et al. |
| 2011/0274675 | A1 | 11/2011 | Stauss et al. |
| 2011/0280889 | A1 | 11/2011 | Schendel et al. |
| 2012/0027739 | A1 | 2/2012 | Jakobsen et al. |
| 2012/0128704 | A1 | 5/2012 | Schendel et al. |
| 2012/0225481 | A1 | 9/2012 | Jakobsen et al. |
| 2012/0252742 | A1 | 10/2012 | Kranz et al. |

(Continued)

FOREIGN PATENT DOCUMENTS

| CN | 101389652 A | 3/2009 |
| CN | 102574906 A | 7/2012 |
| CN | 101389652 B | 5/2013 |

(Continued)

OTHER PUBLICATIONS

Janeway et al., Immunobiology, 5th Ed., Garland Science, 2001, pp. 106-108, 117-118 and 260-263.*
Garcia et al., Cell, 2005, 122: 333-336.*
Busch et al. (Journal of Experimental Medicine, 1999, 189:701-709).*
Holler et al. (Immunity, 2003, 18:255-264).*
Manning et al., Immunity, 1998, 8:413-425.*
International Application No. PCT/US2014/066892, International Search Report and Written Opinion dated Feb. 16, 2015, 11 pages.

(Continued)

*Primary Examiner* — Julie Wu
(74) *Attorney, Agent, or Firm* — Cooley LLP

(57) ABSTRACT

T cell receptors (TCRs) that have specificity for the WT1 antigen are provided. The TCRs include higher affinity TCRs that were engineered through the generation of mutational libraries of TCRs in a single-chain format, followed by selection for improved stability and affinity on the surface of yeast (i.e. directed evolution). In embodiments, the TCRs can be used in soluble form for targeted delivery in vivo, or as genes introduced into T cells in an adoptive T cell setting.

13 Claims, 13 Drawing Sheets

Specification includes a Sequence Listing.

(56) References Cited

U.S. PATENT DOCUMENTS

| | | | |
|---|---|---|---|
| 2013/0273647 A1 | 10/2013 | Sahin et al. | |
| 2016/0280755 A1 | 9/2016 | Smith et al. | |

FOREIGN PATENT DOCUMENTS

| | | |
|---|---|---|
| CN | 103097407 A | 5/2013 |
| CN | 103249430 A | 8/2013 |
| EA | 008026 B1 | 2/2007 |
| JP | 2015-521172 A | 7/2015 |
| WO | WO 2006/129085 A2 | 12/2006 |
| WO | WO 2010/075417 A1 | 7/2010 |
| WO | WO 2013/166321 A1 | 11/2013 |
| WO | WO 2015/077607 A1 | 5/2015 |
| WO | WO 2015/077615 A1 | 5/2015 |
| WO | WO 2016/022400 A1 | 2/2016 |

OTHER PUBLICATIONS

International Application No. PCT/US2014/066892, International Preliminary Report on Patentability dated May 24, 2016, 7 pages.
International Application No. PCT/US2014/066903, International Search Report and Written Opinion dated Feb. 9, 2015, 13 pages.
International Application No. PCT/US2014/066903, International Preliminary Report on Patentability dated May 24, 2016, 8 pages.
Aggen, David H., et al. "Identification and engineering of human variable regions that allow expression of stable single-chain T cell receptors." Protein Engineering Design and Selection (2011); 24.4: 361-372.
Anikeeva, Nadia, et al. "Can oligomeric T-cell receptor be used as a tool to detect viral peptide epitopes on infected cells?." Clinical Immunology (2009); 130.1: 98-109.
Armstrong, Kathryn M., et al. "Conformational changes and flexibility in T-cell receptor recognition of peptide-MHC complexes." Biochemical Journal (2008); 415.2: 183-196.
Ashfield, R. and Jakobsen, B.K. "Making high-affinity T-cell receptors: a new class of targeted therapeutics." IDrugs: The Investigational Drugs Journal (2006); 9.8: 554-559.
Bargou, Ralf, et al. "Tumor regression in cancer patients by very low doses of a T cell-engaging antibody." Science (2008); 321.5891: 974-977.
Benatuil, Lorenzo, et al. "An improved yeast transformation method for the generation of very large human antibody libraries." Protein Engineering Design and Selection (2010); pp. 1-5: gzq002.
Bird, R.E. et al. "Single-chain antigen-binding proteins." Science (1988); 242(4877): 423-426.
Boder, Eric T., et al. "Yeast surface display for screening combinatorial polypeptide libraries." Nature Biotechnology (1997); 15.6: 553-557.
Boder, Eric T., et al. "[25] Yeast surface display for directed evolution of protein expression, affinity, and stability." Methods in Enzymology (2000); 328: 430-444.
Boon, T., and Old, L.J. "Cancer Tumor antigens" Curr Opin Immunol. (1997); 9(5): 681-683.
Borbulevych, Oleg Y., et al. "TCRs used in cancer gene therapy cross-react with MART-1/Melan-A tumor antigens via distinct mechanisms." The Journal of Immunology (2011); 187.5: 2453-2463.
Brower, V. "Enbrel's phase III reinforces prospects in RA." Nat. Biotechnol (1997); 15: 1240, 1 page.
Bulek, Anna M., et al. "Structural basis for the killing of human beta cells by CD8+ T cells in type 1 diabetes." Nature Immunology (2012); 13.3: 283-289, 8 pgs.
Cheever, Martin A., et al. "The prioritization of cancer antigens: a national cancer institute pilot project for the acceleration of translational research." Clinical Cancer Research (2009); 15.17: 5323-5337.
Chervin, Adam S., et al. "Engineering higher affinity T cell receptors using a T cell display system." Journal of Immunological Methods (2008); 339.2: 175-184.

Chervin, A. S., et al. "Design of T-cell receptor libraries with diverse binding properties to examine adoptive T-cell responses." Gene Therapy (2013); 20.6: 634-644.
Colby, David W., et al. "Engineering antibody affinity by yeast surface display." Methods in Enzymology (2004); 388: 348-358.
Davis, M.M., and Bjorkman, P.J. "T-cell antigen receptor genes and T-cell recognition." Nature (1988); 334: 395-402.
Davis, Mark M., et al. "Ligand recognition by alpha beta T cell receptors." Annual Review of Immunology (1998); 16.1: 523-544.
Ding, Yuan-Hua, et al. "Four A6-TCR/peptide/HLA-A2 structures that generate very different T cell signals are nearly identical." Immunity (1999); 11.1: 45-56.
Foote, J. and Eisen, H.N. "Breaking the affinity ceiling for antibodies and T cell receptors." Proceedings of the National Academy of Sciences (2000); 97.20: 10679-10681.
Garboczi, David N., et al. "Structure of the complex between human T-cell receptor, viral peptide and HLA-A2." Nature (1996): 134-141.
Garcia, K. Christopher, et al. "The molecular basis of TCR germline bias for MHC is surprisingly simple." Nature immunology (2009); 10.2: 143-147.
Haidar, Jaafar N., et al. "Structure-based design of a T-cell receptor leads to nearly 100-fold improvement in binding affinity for pepMHC." Proteins: Structure, Function, and Bioinformatics (2009); 74.4: 948-960.
Harkiolaki, Maria, et al. "T cell-mediated autoimmune disease due to low-affinity crossreactivity to common microbial peptides." Immunity (2009); 30.3: 348-357.
Hawse, William F., et al. "Cutting edge: evidence for a dynamically driven T cell signaling mechanism." The Journal of Immunology (2012); 188.12: 5819-5823.
Holler, Phillip D., et al. "TCRs with high affinity for foreign pMHC show self-reactivity." Nature Immunology (2003); 4.1: 55-62. [Published online Dec. 9, 2002].
Holler, Phillip D., et al. "In vitro evolution of a T cell receptor with high affinity for peptide/MHC." Proceedings of the National Academy of Sciences (2000); 97.10: 5387-5392.
Holliger, Philipp., et al. ""Diabodies": small bivalent and bispecific antibody fragments." Proceedings of the National Academy of Sciences (1993); 90.14: 6444-6448.
Hoogenboom, Hennie R. "Selecting and screening recombinant antibody libraries." Nature Biotechnology (2005); 23.9: 1105-1116.
Jarvis, "Rethinking Antibody-Drug Conjugates." Chemical and Engineering News (2012); 12-8.
Kessels, Helmut WHG, et al. "Changing T cell specificity by retroviral T cell receptor display." Proceedings of the National Academy of Sciences (2000); 97.26: 14578-14583.
Kieke, Michele C., et al. "Selection of functional T cell receptor mutants from a yeast surface-display library." Proceedings of the National Academy of Sciences (1999); 96.10: 5651-5656.
Lauck, Florian, et al. "RosettaBackrub—a web server for flexible backbone protein structure modeling and design." Nucleic Acids Research (2010); 38.suppl 2: W569-W575.
Leisegang, Matthias, et al. "MHC-restricted fratricide of human lymphocytes expressing survivin-specific transgenic T cell receptors." The Journal of Clinical Investigation (2010); 120.11: 3869-3877.
Li, Yi, et al. "Directed evolution of human T-cell receptors with picomolar affinities by phage display." Nature Biotechnology (2005); 23.3: 349-354.
Liddy, Nathaniel, et al. "Monoclonal TCR-redirected tumor cell killing." Nature Medicine (2012); 18.6: 980-987.
Litvak-Greenfeld, D. and Benhar, I. "Risks and untoward toxicities of antibody-based immunoconjugates." Advanced Drug Delivery Reviews (2012); 64.15: 1782-1799.
Manning, T.C., and Kranz, D.M. "Binding energetics of T-cell receptors: correlation with immunological consequences." Immunology Today (1999); 20.9: 417-422.
Marrack, Philippa, et al. "Evolutionarily conserved amino acids in TCR V regions and MHC control their interaction." Annual Review of Immunology (2008); 26: 171.

(56) References Cited

OTHER PUBLICATIONS

Mason, D. "A very high level of crossreactivity is an essential feature of the T-cell receptor." Immunology Today (1998); 19: 395-404.
Miller, Brian R., et al. "Stability engineering of scFvs for the development of bispecific and multivalent antibodies." Protein Engineering Design and Selection (2010); 23.7: 549-557.
Molloy, Peter E., et al. "Soluble T cell receptors: novel immunotherapies." Current Opinion in Pharmacology (2005); 5.4: 438-443.
Nold, Marcel F., et al. "IL-37 is a fundamental inhibitor of innate immunity." Nature Immunology (2010); 11.11: 1014-1022.
Pastan, Ira, et al. "Immunotoxin therapy of cancer." Nature Reviews Cancer (2006); 6.7: 559-565.
Pierce, Brian G., et al. "Combinations of affinity-enhancing mutations in a T cell receptor reveal highly nonadditive effects within and between complementarity determining regions and chains." Biochemistry (2010); 49.33: 7050-7059.
Porter, David L., et al. "Chimeric antigen receptor-modified T cells in chronic lymphoid leukemia." New England Journal of Medicine (2011); 365.8: 725-733.
Reichert, J.M. and Valge-Archer, V.E. "Development trends for monoclonal antibody cancer therapeutics." Nature Reviews Drug Discovery (2007); 6.5: 349-356.
Ricart, A.D. and Tolcher, A.W. "Technology insight: cytotoxic drug immunoconjugates for cancer therapy." Nature Clinical Practice Oncology (2007); 4.4: 245-255.
Richman, S.A., et al. "Structural features of T cell receptor variable regions that enhance domain stability and enable expression as single-chain ValphaVbeta fragments." Mol Immunol (2009); 46: 902-916.
Richman, Sarah A., and Kranz, David M. "Display, engineering, and applications of antigen-specific T cell receptors." Biomolecular Engineering (2007); 24.4: 361-373.
Rock, K.L. and Goldberg, A.L. "Degradation of cell proteins and the generation of MHC class I-presented peptides." Annual Review of Immunology (1999); 17.1: 739-779.
Rudolph, Markus G., et al. "How TCRs bind MHCs, peptides, and coreceptors." Annu. Rev. Immunol. (2006); 24: 419-466.
Sadelain, M., et al. "The promise and potential pitfalls of chimeric antigen receptors." Curr Opin Immunol (2009); 21: 215-23.
Sami, Malkit, et al. "Crystal structures of high affinity human T-cell receptors bound to peptide major histocompatibility complex reveal native diagonal binding geometry." Protein Engineering Design and Selection (2007); 20.8: 397-403.
Schrama, David, et al. "Antibody targeted drugs as cancer therapeutics." Nature Reviews Drug Discovery (2006); 5.2: 147-159.
Scott, Jamie K., et al. "Searching for peptide ligands with an epitope library." Science (1990); 249.4967: 386-390.
Skowera, Ania, et al. "CTLs are targeted to kill β cells in patients with type 1 diabetes through recognition of a glucose-regulated preproinsulin epitope." The Journal of Clinical Investigation (2008); 118.10: 3390-3402.
Smith, Colin A., et al. "Backrub-like backbone simulation recapitulates natural protein conformational variability and improves mutant side-chain prediction." Journal of Molecular Biology (2008); 380.4: 742-756.
Hoo, W. F., et al. "Characterization of a single-chain T-cell receptor expressed in *Escherichia coli*." Proceedings of the National Academy of Sciences (1992); 89.10: 4759-4763.
Starr, Timothy., et al. "Positive and negative selection of T cells." Annual Review of Immunology (2003); 21.1: 139-176.
Starwalt, Scott E., et al. "Directed evolution of a single-chain class II MHC product by yeast display." Protein Engineering (2003); 16.2: 147-156.
Stone, J. D., et al. "Engineering High-Affinity T Cell Receptor/Cytokine Fusions for Therapeutic Targeting" In Protein Engineering (2012) (Edited by Kaumaya P.), www.intechopen.com.
Stone, J. D., and Kranz, D. M. "Role of T cell receptor affinity in the efficacy and specificity of adoptive T cell therapies." Front Immunol (2013); 4: 244; pp. 1-16. PMID: 23970885.
Stroncek, David F., et al. "New directions in cellular therapy of cancer: a summary of the summit on cellular therapy for cancer." Journal of Translational Medicine (2012); 10.1: 1.
Swers, Jeffrey S., et al. "Shuffled antibody libraries created by in vivo homologous recombination and yeast surface display." Nucleic Acids Research (2004); 32.3: e36-e36.
Tayal, Vandana, and Kalra, Bhupinder Singh. "Cytokines and anti-cytokines as therapeutics—an update." European Journal of Pharmacology (2008); 579.1: 1-12.
Thakur, Archana, et al. "Cancer therapy with bispecific antibodies: Clinical experience." Current Opinion in Molecular Therapeutics (2010); 12.3: 340.
Tonegawa, Susumu. "Somatic generation of immune diversity." Bioscience Reports (1988); 8.1: 3-26.
Tsomides, Theodore J., et al. "Naturally processed viral peptides recognized by cytotoxic T lymphocytes on cells chronically infected by human immunodeficiency virus type 1." The Journal of Experimental Medicine (1994); 180.4: 1283-1293.
Turner, Damian, et al. "Importance of the linker in expression of single-chain Fv antibody fragments: optimisation of peptide sequence using phage display technology." Journal of Immunological Methods (1997); 205.1: 43-54.
Utz, Ursula, et al. "Analysis of the T-cell receptor repertoire of human T-cell leukemia virus type 1 (HTLV-1) Tax-specific CD8+ cytotoxic T lymphocytes from patients with HTLV-1-associated disease: evidence for oligoclonal expansion." Journal of Virology (1996); 70.2: 843-851.
Varela-Rohena, Angel, et al. "Control of HIV-1 immune escape by CD8 T cells expressing enhanced T-cell receptor." Nature Medicine (2008); 14.12: 1390-1395.
Weber, K. Scott, et al. "Class II-restricted T cell receptor engineered in vitro for higher affinity retains peptide specificity and function." Proceedings of the National Academy of Sciences of the United States of America (2005); 102.52: 19033-19038.
Wong, Richard L., et al. "Interleukin-15: Interleukin-15 receptor α scaffold for creation of multivalent targeted immune molecules." Protein Engineering Design and Selection (2011); 24.4: 373-383.
Aggen, David Henry, "Engineering Human Single-Chain T Cell Receptors," Dissertation, University of Illinois at Urbana-Champaign, 2010, 181 pages.
European Patent Application No. 14864079.0, Extended European Search Report dated Apr. 3, 2017, 8 pages.
European Patent Application No. 14863490.0, Extended European Search Report dated Apr. 3, 2017, 8 pages.
Smith, Sheena A., et al., "Engineering high-affinity human single-chain T cell receptors against cancer antigens", Jan. 1, 2013, XP055348950, 1 page, Retrieved from the Internet: URL:http://www.medigene.de/fileadmin/download/abstracts/22_smith_-engineering_high-affinity_human_singlechain_t_cell_receptors_keystone2013.pdf [retrieved on Mar. 23, 2017].
Bowerman et al., "Engineering the binding properties of the T cell receptor: peptide: MHC ternary complex that governs T cell activity." Molecular Immunology (2009); 46 (15): 3000-3008.
Dossett et al., "Adoptive immunotherapy of disseminated leukemia with TCR-transduced, CD8+ T cells expressing a known endogenous TCR," Mol Ther., Apr. 2009; 17(4):742-9.
Falkenburg et al., "Allogeneic HLA-A*02-Restricted WT1-Specific T Cells from Mismatched Donors Are Highly Reactive but Show Off-Target Promiscuity," J Immunol, Sep. 1, 2011, 187 (5) pp. 2824-2833.
Schendel et al. "Limitations for TCR gene therapy by MHC-restricted fratricide and TCR-mediated hematopoietic stem cell toxicity," Oncolmmunology 2:1, e22410; Jan. 2013.
Schmitt et al., "Enhanced-affinity murine T-cell receptors for tumor/self-antigens can be safe in gene therapy despite surpassing the threshold for thymic selection," Blood, Jul. 18, 2013; 122(3): 348-356.
Shen et al. "Identification of a novel HLA-A2-restricted mutated Survivin epitope and induction of specific anti-HCC CTLs that

(56) References Cited

OTHER PUBLICATIONS could effectively cross-recognize wild-type Survivin antigen," Cancer Immunology Immunotherapy, 2013 (Published online: Aug. 29, 2012), 62: 393-403.

Stauss et al., "WT1-specific T cell receptor gene therapy: Improving TCR function in transduced T cells," Blood Cells, Molecules, and Diseases, 40 (2008) pp. 113-116.

Stone et al., "T-cell receptor binding affinities and kinetics: impact on T-cell activity and specificity." Immunology (2009); 126 (2): 165-176.

* cited by examiner

FIG. 1

SEQUENCE LISTING

```
<160> NUMBER OF SEQ ID NOS: 34

<210> SEQ ID NO 1
<211> LENGTH: 115
<212> TYPE: PRT
<213> ORGANISM: Homo sapiens

<400> SEQUENCE: 1

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ser Ile
                85                  90                  95

Asn Glu Gln Phe Phe Gly Pro Gly Thr Arg Leu Thr Val Leu Glu Asp
            100                 105                 110

Leu Lys Asn
        115

<210> SEQ ID NO 2
<211> LENGTH: 112
<212> TYPE: PRT
<213> ORGANISM: Homo sapiens

<400> SEQUENCE: 2

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Val Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Asn Asn Ala Gly Asn
                85                  90                  95

Met Leu Thr Phe Gly Gly Gly Thr Arg Leu Met Val Lys Pro His Ile
            100                 105                 110

<210> SEQ ID NO 3
<211> LENGTH: 115
<212> TYPE: PRT
<213> ORGANISM: Artificial Sequence
<220> FEATURE:
<223> OTHER INFORMATION: Modified variable beta region of the TCR with
      high affinity to WT1/HLA-A2
```

<400> SEQUENCE: 3

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Ser
        35                  40                  45

Ser Tyr Gly Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Thr Ser Asn Tyr
                85                  90                  95

Leu Glu Gln Phe Phe Gly Pro Gly Thr Arg Leu Thr Val Leu Glu Asp
            100                 105                 110

Leu Lys Asn
        115

<210> SEQ ID NO 4
<211> LENGTH: 112
<212> TYPE: PRT
<213> ORGANISM: Artificial Sequence
<220> FEATURE:
<223> OTHER INFORMATION: Modified variable alpha region of the TCR with
      high affinity to WT1/HLA-A2

<400> SEQUENCE: 4

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Asp Leu Gly Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Asn Asn Ala Gly Asn
                85                  90                  95

Met Leu Thr Phe Gly Gly Gly Thr Arg Leu Met Val Lys Pro His Ile
            100                 105                 110

<210> SEQ ID NO 5
<211> LENGTH: 244
<212> TYPE: PRT
<213> ORGANISM: Artificial Sequence
<220> FEATURE:
<223> OTHER INFORMATION: Single-chain TCR that binds with high-affinity
      to WT1/HLA-A2

<400> SEQUENCE: 5

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Ser
        35                  40                  45

```
Ser Tyr Gly Val Lys Met Lys Glu Lys Gly Asp Ile Pro Glu Gly Tyr
    50                  55                  60
Ser Val Ser Arg Glu Lys Lys Glu Arg Phe Ser Leu Ile Leu Glu Ser
65                  70                  75                  80
Ala Ser Thr Asn Gln Thr Ser Met Tyr Leu Cys Ala Thr Ser Asn Tyr
                85                  90                  95
Leu Glu Gln Phe Phe Gly Pro Gly Thr Arg Leu Thr Val Leu Glu Asp
            100                 105                 110
Leu Lys Asn Gly Ser Ala Asp Asp Ala Lys Lys Asp Ala Ala Lys Lys
        115                 120                 125
Asp Gly Lys Ser Gln Lys Glu Val Glu Gln Asn Ser Gly Pro Leu Ser
    130                 135                 140
Val Pro Glu Gly Ala Ile Ala Ser Leu Asn Cys Thr Tyr Ser Asp Arg
145                 150                 155                 160
Asp Leu Gly Ser Phe Phe Trp Tyr Arg Gln Tyr Ser Gly Lys Ser Pro
                165                 170                 175
Glu Leu Ile Met Ser Ile Tyr Ser Asn Gly Asp Lys Glu Asp Gly Arg
            180                 185                 190
Phe Thr Ala Gln Leu Asn Lys Ala Ser Gln Tyr Val Ser Leu Leu Ile
        195                 200                 205
Arg Asp Ser Gln Pro Ser Asp Ser Ala Thr Tyr Leu Cys Ala Ala Asn
    210                 215                 220
Asn Ala Gly Asn Met Leu Thr Phe Gly Gly Gly Thr Arg Leu Met Val
225                 230                 235                 240
Lys Pro His Ile

<210> SEQ ID NO 6
<211> LENGTH: 9
<212> TYPE: PRT
<213> ORGANISM: Homo sapiens

<400> SEQUENCE: 6

Arg Met Phe Pro Asn Ala Pro Tyr Leu
1               5

<210> SEQ ID NO 7
<211> LENGTH: 9
<212> TYPE: PRT
<213> ORGANISM: Human T cell lymphotrophic virus

<400> SEQUENCE: 7

Leu Leu Phe Gly Tyr Pro Val Tyr Val
1               5

<210> SEQ ID NO 8
<211> LENGTH: 17
<212> TYPE: PRT
<213> ORGANISM: Artificial Sequence
<220> FEATURE:
<223> OTHER INFORMATION: Amino acid linker sequence

<400> SEQUENCE: 8

Gly Ser Ala Asp Asp Ala Lys Lys Asp Ala Ala Lys Lys Asp Gly Lys
1               5                   10                  15
Ser

<210> SEQ ID NO 9
<211> LENGTH: 24
<212> TYPE: DNA
```

<213> ORGANISM: Artificial Sequence
<220> FEATURE:
<223> OTHER INFORMATION: Primer Splice 4L

<400> SEQUENCE: 9
ggcagcccca taaacacaca gtat                                        24

<210> SEQ ID NO 10
<211> LENGTH: 63
<212> TYPE: DNA
<213> ORGANISM: Artificial Sequence
<220> FEATURE:
<223> OTHER INFORMATION: Reverse primer used to generate the WT1-D13
      CDR1alpha library

<400> SEQUENCE: 10
acgatcgcta taggtgcagt tcaatgatgc aatagcacct tccgggacac ttaatgggcc    60
gct                                                                 63

<210> SEQ ID NO 11
<211> LENGTH: 81
<212> TYPE: DNA
<213> ORGANISM: Artificial Sequence
<220> FEATURE:
<223> OTHER INFORMATION: Forward primer used to generate the WT1-D13
      CDR1alpha library
<220> FEATURE:
<221> NAME/KEY: misc_feature
<222> LOCATION: (34)..(35)
<223> OTHER INFORMATION: n = any base
<220> FEATURE:
<221> NAME/KEY: misc_feature
<222> LOCATION: (37)..(38)
<223> OTHER INFORMATION: n = any base
<220> FEATURE:
<221> NAME/KEY: misc_feature
<222> LOCATION: (40)..(41)
<223> OTHER INFORMATION: n = any base
<220> FEATURE:
<221> NAME/KEY: misc_feature
<222> LOCATION: (43)..(44)
<223> OTHER INFORMATION: n = any base

<400> SEQUENCE: 11
attgcatcat tgaactgcac ctatagcgat cgtnnsnnsn nsnnsttctt ttggtataga    60
cagtacagtg gcaaatcccc g                                             81

<210> SEQ ID NO 12
<211> LENGTH: 20
<212> TYPE: DNA
<213> ORGANISM: Artificial Sequence
<220> FEATURE:
<223> OTHER INFORMATION: Primer T7

<400> SEQUENCE: 12
taatacgact cactataggg                                               20

<210> SEQ ID NO 13
<211> LENGTH: 66
<212> TYPE: DNA
<213> ORGANISM: Artificial Sequence
<220> FEATURE:
<223> OTHER INFORMATION: Reverse primer used to generate the WT1-D13.1
      CDR3 beta1 library

<400> SEQUENCE: 13
tgcacacagg tacatggaag tttgattggt actagcgctt tccagaatca aactgaaacg    60
ttctttt 66

```
<210> SEQ ID NO 14
<211> LENGTH: 84
<212> TYPE: DNA
<213> ORGANISM: Artificial Sequence
<220> FEATURE:
<223> OTHER INFORMATION: Forward primer used to generate the WT1-D13.1
      CDR3 beta1 library
<220> FEATURE:
<221> NAME/KEY: misc_feature
<222> LOCATION: (34)..(35)
<223> OTHER INFORMATION: n = any base
<220> FEATURE:
<221> NAME/KEY: misc_feature
<222> LOCATION: (37)..(38)
<223> OTHER INFORMATION: n = any base
<220> FEATURE:
<221> NAME/KEY: misc_feature
<222> LOCATION: (40)..(41)
<223> OTHER INFORMATION: n = any base
<220> FEATURE:
<221> NAME/KEY: misc_feature
<222> LOCATION: (43)..(44)
<223> OTHER INFORMATION: n = any base
<220> FEATURE:
<221> NAME/KEY: misc_feature
<222> LOCATION: (46)..(47)
<223> OTHER INFORMATION: n is a, c, g, or t
```

<400> SEQUENCE: 14
agtaccaatc aaacttccat gtacctgtgt gcannsnnsn nsnnsnnsga acagttttc    60 ggcccaggta caagattaac ggtg                                          84

```
<210> SEQ ID NO 15
<211> LENGTH: 66
<212> TYPE: DNA
<213> ORGANISM: Artificial Sequence
<220> FEATURE:
<223> OTHER INFORMATION: Reverse primer used to generate the WT1-D13.1
      CDR3 beta2 library
```

<400> SEQUENCE: 15
tgcacacagg tacatggaag tttgattggt actagcgctt tccagaatca aactgaaacg    60
ttcttt                                                               66

```
<210> SEQ ID NO 16
<211> LENGTH: 84
<212> TYPE: DNA
<213> ORGANISM: Artificial Sequence
<220> FEATURE:
<223> OTHER INFORMATION: Forward primer used to generate theWT1-D13.1
      CDR3 beta2 library
<220> FEATURE:
<221> NAME/KEY: misc_feature
<222> LOCATION: (46)..(47)
<223> OTHER INFORMATION: n = any base
<220> FEATURE:
<221> NAME/KEY: misc_feature
<222> LOCATION: (49)..(50)
<223> OTHER INFORMATION: n = any base
<220> FEATURE:
<221> NAME/KEY: misc_feature
<222> LOCATION: (52)..(53)
<223> OTHER INFORMATION: n = any base
<220> FEATURE:
<221> NAME/KEY: misc_feature
<222> LOCATION: (55)..(56)
<223> OTHER INFORMATION: n = any base
<220> FEATURE:
<221> NAME/KEY: misc_feature
<222> LOCATION: (58)..(59)
```

<223> OTHER INFORMATION: n is a, c, g, or t

<400> SEQUENCE: 16
agtaccaatc aaacttccat gtacctgtgt gcaagcagtt ccatcnnsnn snnsnnsnns    60
ggcccaggta caagattaac ggtg    84

<210> SEQ ID NO 17
<211> LENGTH: 66
<212> TYPE: DNA
<213> ORGANISM: Artificial Sequence
<220> FEATURE:
<223> OTHER INFORMATION: Reverse primer used to generate the WT1-D13.1
      CDR3 alpha1 library

<400> SEQUENCE: 17
ggcgcacagg taagtggcgc tatctgacgg ttggctatca cggattaaca gagagacata    60
ctggga    66

<210> SEQ ID NO 18
<211> LENGTH: 84
<212> TYPE: DNA
<213> ORGANISM: Artificial Sequence
<220> FEATURE:
<223> OTHER INFORMATION: Forward primer used to generate theWT1-D13.1
      CDR3 alpha1 library
<220> FEATURE:
<221> NAME/KEY: misc_feature
<222> LOCATION: (34)..(35)
<223> OTHER INFORMATION: n = any base
<220> FEATURE:
<221> NAME/KEY: misc_feature
<222> LOCATION: (37)..(38)
<223> OTHER INFORMATION: n = any base
<220> FEATURE:
<221> NAME/KEY: misc_feature
<222> LOCATION: (40)..(41)
<223> OTHER INFORMATION: n = any base
<220> FEATURE:
<221> NAME/KEY: misc_feature
<222> LOCATION: (43)..(44)
<223> OTHER INFORMATION: n = any base
<220> FEATURE:
<221> NAME/KEY: misc_feature
<222> LOCATION: (46)..(47)
<223> OTHER INFORMATION: n is a, c, g, or t

<400> SEQUENCE: 18
caaccgtcag atagcgccac ttacctgtgc gccnnsnnsn nsnnsnnsaa tatgctgacc    60
ttcggtggcg gtactcgctt aatg    84

<210> SEQ ID NO 19
<211> LENGTH: 66
<212> TYPE: DNA
<213> ORGANISM: Artificial Sequence
<220> FEATURE:
<223> OTHER INFORMATION: Reverse primer used to generate the WT1-D13.1
      CDR3 alpha2 library

<400> SEQUENCE: 19
ggcgcacagg taagtggcgc tatctgacgg ttggctatca cggattaaca gagagacata    60
ctggga    66

<210> SEQ ID NO 20
<211> LENGTH: 84
<212> TYPE: DNA
<213> ORGANISM: Artificial Sequence
<220> FEATURE:

<223> OTHER INFORMATION: Forward primer used to generate the WT1-D13.1
       CDR3 alpha2 library
<220> FEATURE:
<221> NAME/KEY: misc_feature
<222> LOCATION: (46)..(47)
<223> OTHER INFORMATION: n = any base
<220> FEATURE:
<221> NAME/KEY: misc_feature
<222> LOCATION: (49)..(50)
<223> OTHER INFORMATION: n = any base
<220> FEATURE:
<221> NAME/KEY: misc_feature
<222> LOCATION: (52)..(53)
<223> OTHER INFORMATION: n = any base
<220> FEATURE:
<221> NAME/KEY: misc_feature
<222> LOCATION: (55)..(56)
<223> OTHER INFORMATION: n = any base
<220> FEATURE:
<221> NAME/KEY: misc_feature
<222> LOCATION: (58)..(59)
<223> OTHER INFORMATION: n is a, c, g, or t

<400> SEQUENCE: 20
caaccgtcag atagcgccac ttacctgtgc gccgcgaata acgcgnnsnn snnsnnsnns    60
ttcggtggcg gtactcgctt aatg                                          84

<210> SEQ ID NO 21
<211> LENGTH: 115
<212> TYPE: PRT
<213> ORGANISM: Artificial Sequence
<220> FEATURE:
<223> OTHER INFORMATION: Modified variable beta region of the TCR with
      high affinity to WT1/HLA-A2

<400> SEQUENCE: 21

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Ser
        35                  40                  45

Ser Tyr Gly Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Ile
                85                  90                  95

Asn Glu Gln Phe Phe Gly Pro Gly Thr Arg Leu Thr Val Leu Glu Asp
            100                 105                 110

Leu Lys Asn
        115

<210> SEQ ID NO 22
<211> LENGTH: 112
<212> TYPE: PRT
<213> ORGANISM: Artificial Sequence
<220> FEATURE:
<223> OTHER INFORMATION: Modified variable alpha region of the TCR with
      high affinity to WT1/HLA-A2

<400> SEQUENCE: 22

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Val Ser Gln Pro

```
                    20                  25                  30
Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
        50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Asn Asn Ala Gly Asn
                85                  90                  95

Met Leu Thr Phe Gly Gly Gly Thr Arg Leu Met Val Lys Pro His Ile
            100                 105                 110
```

<210> SEQ ID NO 23
<211> LENGTH: 9
<212> TYPE: PRT
<213> ORGANISM: Influenza A

<400> SEQUENCE: 23

```
Ala Ser Asn Glu Asn Met Asp Ala Met
1               5
```

<210> SEQ ID NO 24
<211> LENGTH: 9
<212> TYPE: PRT
<213> ORGANISM: Influenza A

<400> SEQUENCE: 24

```
Ala Ser Asn Glu Asn Met Glu Thr Met
1               5
```

<210> SEQ ID NO 25
<211> LENGTH: 9
<212> TYPE: PRT
<213> ORGANISM: Artificial Sequence
<220> FEATURE:
<223> OTHER INFORMATION: WT1 structurally similar human peptide

<400> SEQUENCE: 25

```
Lys Leu Phe Ser Gln Leu Ser Tyr Leu
1               5
```

<210> SEQ ID NO 26
<211> LENGTH: 9
<212> TYPE: PRT
<213> ORGANISM: Artificial Sequence
<220> FEATURE:
<223> OTHER INFORMATION: WT1 structurally similar human peptide

<400> SEQUENCE: 26

```
Lys Leu Phe Ser Thr Ala Met Phe Leu
1               5
```

<210> SEQ ID NO 27
<211> LENGTH: 9
<212> TYPE: PRT
<213> ORGANISM: Artificial Sequence
<220> FEATURE:
<223> OTHER INFORMATION: WT1 structurally similar human peptide

<400> SEQUENCE: 27

```
His Met Trp Gly Gln Ser Leu Tyr Ile
1               5
```

```
<210> SEQ ID NO 28
<211> LENGTH: 9
<212> TYPE: PRT
<213> ORGANISM: Artificial Sequence
<220> FEATURE:
<223> OTHER INFORMATION: WT1 structurally similar human peptide

<400> SEQUENCE: 28

Lys Ile Phe Gly Ser Leu Ala Phe Leu
1               5

<210> SEQ ID NO 29
<211> LENGTH: 9
<212> TYPE: PRT
<213> ORGANISM: Artificial Sequence
<220> FEATURE:
<223> OTHER INFORMATION: WT1 structurally similar human peptide

<400> SEQUENCE: 29

Lys Ile Phe Pro Ser Cys Leu Phe Val
1               5

<210> SEQ ID NO 30
<211> LENGTH: 9
<212> TYPE: PRT
<213> ORGANISM: Artificial Sequence
<220> FEATURE:
<223> OTHER INFORMATION: WT1 structurally similar human peptide

<400> SEQUENCE: 30

Lys Leu Trp Pro Ser Val Ala Phe Ala
1               5

<210> SEQ ID NO 31
<211> LENGTH: 9
<212> TYPE: PRT
<213> ORGANISM: Artificial Sequence
<220> FEATURE:
<223> OTHER INFORMATION: WT1 structurally similar human peptide

<400> SEQUENCE: 31

His Leu Trp Gly Gln Ser Leu Tyr Ile
1               5

<210> SEQ ID NO 32
<211> LENGTH: 9
<212> TYPE: PRT
<213> ORGANISM: Artificial Sequence
<220> FEATURE:
<223> OTHER INFORMATION: WT1 structurally similar human peptide

<400> SEQUENCE: 32

Arg Ile Trp Leu Ser Val Val Phe Val
1               5

<210> SEQ ID NO 33
<211> LENGTH: 9
<212> TYPE: PRT
<213> ORGANISM: Artificial Sequence
<220> FEATURE:
<223> OTHER INFORMATION: WT1 structurally similar human peptide

<400> SEQUENCE: 33

His Leu Phe Ser Ser Leu Pro Phe Ala
1               5

<210> SEQ ID NO 34
```

```
<211> LENGTH: 9
<212> TYPE: PRT
<213> ORGANISM: Artificial Sequence
<220> FEATURE:
<223> OTHER INFORMATION: WT1 structurally similar human peptide

<400> SEQUENCE: 34

Arg Ile Phe Ser Thr Ala Leu Phe Val
1               5
```

ENGINEERED HIGH-AFFINITY HUMAN T CELL RECEPTORS

CROSS-REFERENCE TO RELATED APPLICATIONS

This application is a 371 of international application number PCT/US2014/066903, filed Nov. 21, 2014, which claims the benefit under 35 U.S.C. § 119(e) of U.S. Provisional Patent Application No. 61/907,887, filed Nov. 22, 2013, each of which applications are incorporated herein by reference in their entirety.

STATEMENT REGARDING FEDERALLY SPONSORED RESEARCH OR DEVELOPMENT

This disclosure was made with U.S. Government support under Grant numbers R01 GM55767 and T32 GM070421, awarded by the National Institutes of Health. The U.S. Government has certain rights in the disclosure.

STATEMENT REGARDING SEQUENCE LISTING

The Sequence Listing associated with this application is provided in text format in lieu of a paper copy, and is hereby incorporated by reference into the specification. The name of the text file containing the Sequence Listing is IMMU_003_02WO_ST25.txt. The text file is 18 KB, was created on Nov. 21, 2014 and is being submitted electronically via EFS-Web.

FIELD OF THE INVENTION

The disclosure relates to T cell receptors (TCR) against the Wilms' tumor antigen (WT1), including high-affinity TCRs engineered by in vitro techniques, as well as methods of producing modified TCRs and single-chain TCRs and the corresponding uses of the TCRs for therapeutic, diagnostic, and imaging methods.

BACKGROUND

T cell receptors (TCRs) and antibodies are molecules that have evolved to recognize different classes of antigens (ligands)((Murphy (2012), xix, 868 p.)). TCRs are antigen-specific molecules that are responsible for recognizing antigenic peptides presented in the context of a product of the major histocompatibility complex (MHC) on the surface of antigen presenting cells (APCs) or any nucleated cell (e.g., all human cells in the body, except red blood cells). In contrast, antibodies typically recognize soluble or cell-surface antigens, and do not require presentation of the antigen by an MHC. This system endows T cells, via their TCRs, with the potential ability to recognize the entire array of intracellular antigens expressed by a cell (including virus proteins) that are processed intracellularly into short peptides, bound to an intracellular MHC molecule, and delivered to the surface as a peptide-MHC complex (pepMHC). This system allows virtually any foreign protein (e.g., mutated cancer antigen or virus protein) or aberrantly expressed protein to serve a target for T cells (reviewed in (Davis and Bjorkman (1988) Nature, 334, 395-402; Davis et al. (1998) Annu Rev Immunol, 16, 523-544; Murphy (2012), xix, 868 p.)).

The interaction of a TCR and a pepMHC can drive the T cell into various states of activation, depending on the affinity (or dissociation rate) of binding. The TCR recognition process allows a T cell to discriminate between a normal, healthy cell and, e.g., one that has become transformed via a virus or malignancy, by providing a diverse repertoire of TCRs, wherein there is a high probability that one or more TCRs will be present with a binding affinity for the foreign peptide bound to an MHC molecule that is above the threshold for stimulating T cell activity (Manning and Kranz (1999) Immunology Today, 20, 417-422).

To date, wild type TCRs isolated from either human or mouse T cell clones that were identified by in vitro culturing have been shown to have relatively low binding affinities ($K_d$=1-300 μM) (Davis et al. (1998) Annu Rev Immunol, 16, 523-544). Part of the explanation for this seems to be that T cells that develop in the thymus are negatively selected (tolerance induction) on self-pepMHC ligands, such that T cells with too high of an affinity are deleted (Starr et al. (2003) Annu Rev Immunol, 21, 139-76). To compensate for these relatively low affinities, T cells have evolved a co-receptor system in which the cell surface molecules CD4 and CD8 bind to the MHC molecules (class II and class I, respectively) and synergize with the TCR in mediating signaling activity. CD8 is particularly effective in this process, allowing TCRs with very low affinity (e.g., $K_d$=300 μM) to mediate potent antigen-specific activity.

In vitro, directed evolution has been used to generate TCRs with higher affinity for a specific pepMHC. The three different display methods that have been used are yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), and T cell display (Chervin et al. (2008) J Immunol Methods, 339, 175-84). In all three approaches, the process involves engineering, or modifying, a TCR that exhibits the normal, low affinity of the wild-type TCR, so that affinity of mutants of the TCR have increased affinity for the cognate pepMHC (the original antigen that the T cells were specific for). Thus, the wild-type TCR was used as a template for producing mutagenized libraries in one or more of the CDRs, and mutants with higher affinity were selected by binding to the cognate peptide-MHC antigen.

In the present disclosure, a wild-type T cell receptor and high affinity T cell receptors specific for the Wilm's Tumor-1 (WT1) engineered by yeast display are disclosed. WT1 is a transcription factor that has been described to function both as a tumor suppressor and an oncogene. WT1 is expressed at high levels in leukemia as well as a variety of solid tumors (Sugiyama et al. (2010) *Japanese Journal of Clinical Oncology* 40(5) 377-387). It has been the target of vaccine efforts, and various adoptive T cell approaches using T cells with wild-type T cell receptors.

WT1 has been ranked number 1 in a prioritization list of the top 75 cancer antigens by the National Cancer Institute (Cheever et al. (2009) Clin Cancer Res, 15, 5323-5337). Accordingly, there is a need to identify agents, e.g., therapeutic agents, that specifically target this cancer antigen. The present invention provides in vitro engineered, higher affinity TCRs that can be used, e.g., in soluble form for targeted delivery in vivo or as genes introduced into T cells in an adoptive T cell setting.

SUMMARY OF THE INVENTION

The present invention relates to a wild-type T cell receptor against the WT1 antigen, and in vitro engineered T cell receptors (TCR) that bind to the WT1 antigen with improved affinity. More specifically, the present disclosure relates to the sequences of the wild-type T cell receptor and those stabilizing and affinity mutations selected through the display of libraries on the surface of yeast, phage, or mammalian cells; to TCR proteins selected from these libraries for binding to an antigen with increased affinity; and to the use of in vitro selected TCR derivatives for therapeutic, diagnostic, or imaging applications.

One aspect of the invention relates to a T cell receptor, or antigen-binding fragment thereof, comprising a Vα and a Vβ derived from a T cell clone, wherein the T cell receptor binds to a complex of the peptide WT1 and the HLA-A2 molecule, and wherein the T cell receptor comprises the Vβ amino acid sequence set forth in SEQ ID NO:1 and the Vα amino acid sequence set forth in SEQ ID NO:2. In one embodiment, a host cell that expresses the T cell receptor. In a further embodiment, the host cell is a human T cell.

One aspect of the invention elates to a modified T cell receptor, or antigen binding fragment thereof, comprising a Vα and a Vβ derived from a wild type T cell receptor, wherein the Vα, the Vβ, or both, comprise a mutation in one or more complementarity determining regions (CDRs) relative to the wild type T cell receptor, wherein the modified T cell receptor binds to the peptide/MHC antigen known as WT1/HLA-A2 (the WT1 peptide RMFPNAPYL (SEQ ID NO:6), bound to the MHC product known as HLA-A2).

In one embodiment, the T cell receptor comprises a Vβ comprising an amino acid sequence having at least 80% identity to the Vβ amino acid sequence set forth in SEQ ID NO:1, wherein the T cell receptor mediates activity by binding to WT1/HLA-A2.

In another embodiment, the modified T cell receptor comprises a modified Vβ comprising an amino acid sequence having at least 80% identity to the Vβ amino acid sequence set forth in SEQ ID NO:3, wherein the modified T cell receptor binds to WT1/HLA-A2 with an affinity ($K_A$ value) of $10^6$ M higher.

In another embodiment, the T cell receptor comprises a Vα comprising an amino acid sequence having at least 80% identity to the Vα amino acid sequence set forth in SEQ ID NO:2, wherein the T cell receptor mediates activity by binding to WT1/HLA-A2.

In another embodiment, the modified T cell receptor comprises a modified Vα comprising an amino acid sequence having at least 80% identity to the Vα amino acid sequence set forth in SEQ ID NO:4, wherein the modified T cell receptor binds to WT1/HLA-A2 with an affinity ($K_A$ value) of $10^6$ M higher.

In one embodiment, the T cell receptor is a single-chain T cell receptor comprising the amino acid sequence set forth in SEQ ID NO:5.

In one embodiment, the T cell receptor contains at least one of the mutations in CDR3β selected from S95T, S97N, I103Y, N104L of the amino acid sequence set forth in SEQ ID NO:3.

In another embodiment, the T cell receptor contains at least one of the mutations in CDR1α selected from V29D, S30L, and Q31G of the amino acid sequence set forth in SEQ ID NO:4.

In one embodiment, the modified T cell receptor is generated by in vitro selection of a yeast display library of mutant T cell receptors.

In another embodiment, the modified T cell receptor is expressed as a soluble protein that binds to its target antigen.

In another embodiment, the wild-type or the modified T cell receptors are expressed in T cells for adoptive T cell therapies.

One aspect of the invention provides a therapeutic agent that targets cancer cells that express the WT1 antigen, wherein the therapeutic agent comprises a modified T cell receptor described herein. In one embodiment, a therapeutic agent that targets cancer cells that express the WT1 antigen, wherein the therapeutic agent comprises a human T cell that expresses a modified T cell receptor described herein. One embodiment provides a method of treating a subject having a cancer that expresses the WT1 antigen comprising administering a therapeutic agent described herein.

BRIEF DESCRIPTION OF THE DRAWINGS

Figure 1:
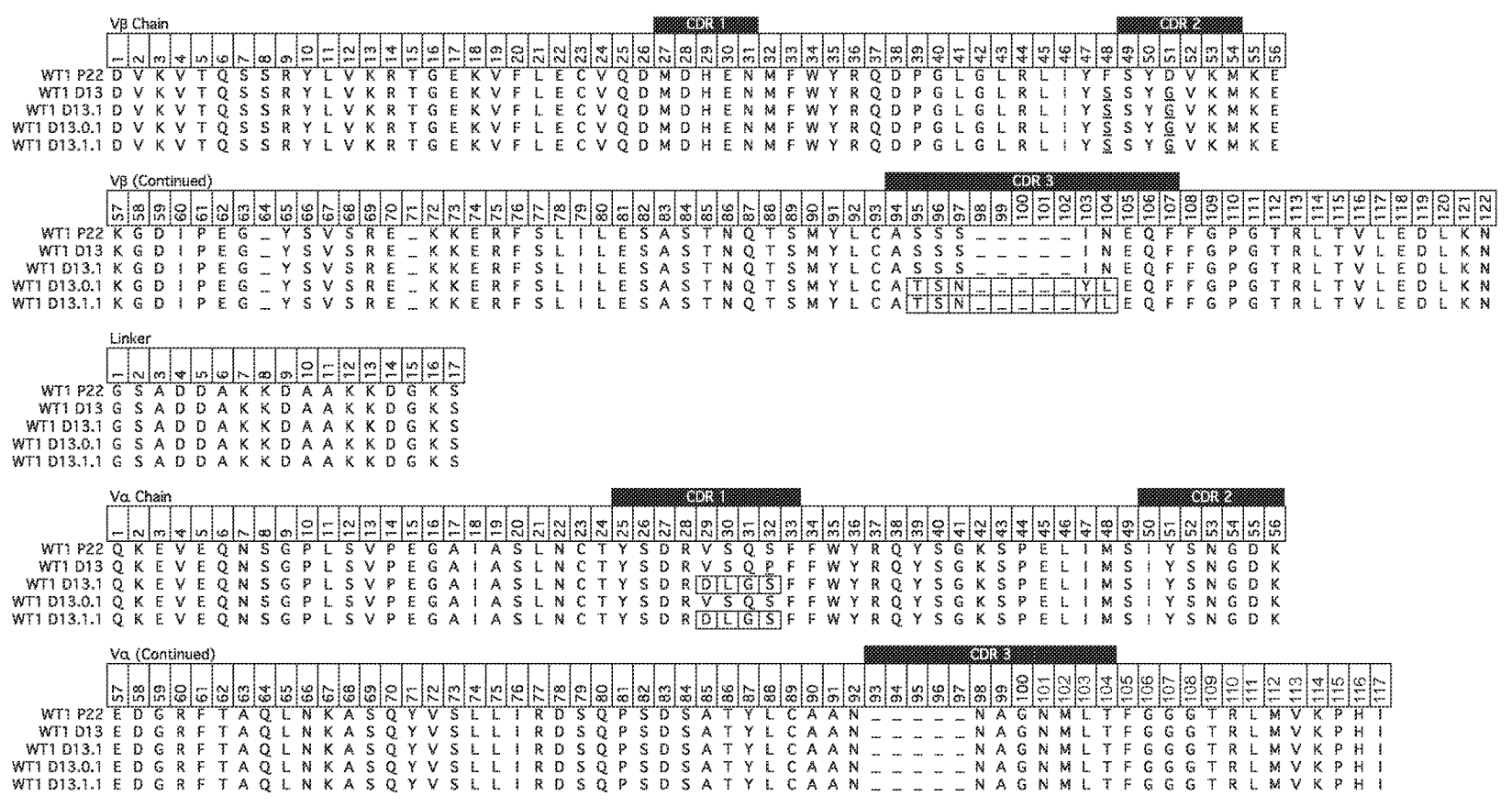

FIG. 1 shows the aligned amino acid sequences of various WT1/HLA-A2 specific T cell receptors from the present study. WT1 P22 represents the wild-type sequence isolated from a human T cell clone that was stimulated by WT1/HLA-A2. The other TCR sequences were isolated by yeast display methods for greater surface levels and for higher affinities. The amino acid residues within the CDR3β and the CDR1α that are highlighted within rectangles were mutations in TCRs isolated for higher affinity by yeast display. The sequences shown for the Vβ chain correspond to SEQ ID NOs:1, 21, 21, 3, and 3, from top to bottom. The linker sequence depicted is SEQ ID NO:8. The sequences shown for the Vα chain correspond to SEQ ID NOs:2, 22, 4, 2, and 4, from top to bottom.

FIG. 8A shows the flow cytometry histograms of the high affinity scTCR WT1 D13.1.1 stained with various concentrations of WT1:HLA-A2 Ig dimer, followed by fluorescent labeled anti-Ig antibody as a secondary. FIG. 8B shows the flow cytometry histograms of the high affinity scTCR WT1 D13.1.1 stained with various concentrations of biotinylated WT1:HLA-A2 monomer, followed by SA-PE (1:100) secondary. FIG. 8C is a line graph that shows mean fluorescence intensity (MFI) values of histograms in FIG. 7A plotted versus WT1:HLA-A2 dimer concentration. FIG. 8D is a line graph that shows mean fluorescence intensity (MFI) values of histograms in FIG. 8B plotted versus WT1:HLA-A2 monomer concentration.

FIGS. 9A-D are a series of histograms that show flow cytometry analysis of human T2 (HLA-A2+) cells incubated first with no peptide (FIG. 9A), negative control peptide Tax (FIG. 9B), negative control peptide MART-1 (FIG. 9C), or peptide WT1 (FIG. 9D), followed by incubation with biotin-labeled WT1-D13.1.1 TCR. FIG. 9E is a graph that depicts the titration showing that the WT1-D13.1.1 TCR had a minimum affinity ($K_D$ value) of at least 260 nM (as washing of cells in flow cytometry results in an underestimate of affinities in this range).

FIG. 12A depicts five examples of TCR formats for use as soluble therapeutic products: 1) single-chain TCR in either a Vα-Vβ orientation or Vβ-Vα orientation (mutated high-affinity V domains are shown with an asterisk); 2) single-chain TCR fused in frame with the constant region domains of an antibody; 3) in-frame immunoglobulin fusion to either the constant region of the light chain or the heavy chain; 4) single-chain TCR (or the immunoglobulin fusions shown in 2 and 3) directly coupled to a drug; and 5) single-chain TCR linked in-frame with a single-chain Fv (VL-linker-VH) to generate a bispecific agent. FIG. 12B depicts two examples of cellular based therapies that would use the high-affinity variable domains (V) isolated by yeast display, or the wild-type TCR V domains may also be used for adoptive T cell therapies with human T cells). The TCRs are cloned into mammalian cell vectors, for expression by T cells in adoptive T cell therapy as: 1) single-chain receptors in chimeric antigen receptors (CAR) and 2) full length α and β TCRs.

BRIEF DESCRIPTION OF THE SEQUENCES

Figure 2:
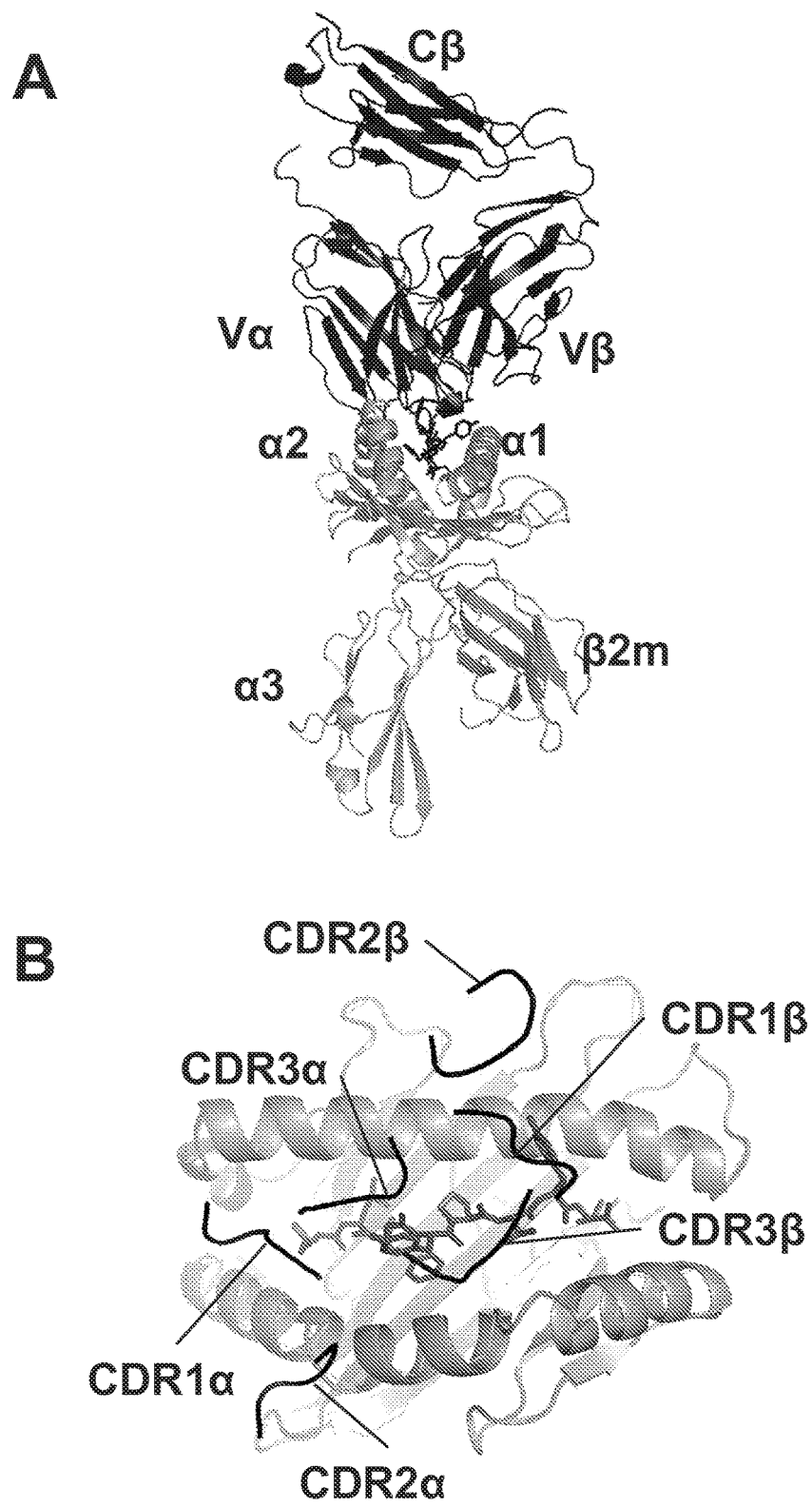
FIG. 2A is a 3-dimensional diagram that shows a side view of the TCR:pepMHC complex (A6; PDB:1AO7). The variable (V) and constant (C) regions of the α-chain and β-chain are indicated. The structure shown does not include the Cα region of the TCR. HLA-A2 (α1, α2, α3, and Bβ2m) is shown in gray, and the Tax peptide (LLFGYPVYV, SEQ ID NO:7) is shown in black. The A6 TCR and the WT1 TCRs examined in the present invention all use the Vα2 segment (also referred to as TRAV12 based on IMGT nomenclature).
FIG. 2B is a 3-dimensional diagram that shows the top down view of the TCR (CDR) footprint over the peptide-MHC (Tax/HLA-A2). Although no crystal structures have been described for the WT1 TCR used in the present disclosure, this diagonal docking orientation, with the Vα region positioned over the α2 MHC helix and the N-terminal end of the peptide, and the Vβ region positioned over the α1 MHC helix and C-terminal end of the peptide, has been observed in virtually all complexes to date.

SEQ ID NO:1 is the amino acid sequence of a wild-type Vβ region of the TCR (P22) that binds to WT1/HLA-A2.

SEQ ID NO:2 is the amino acid sequence of a wild-type Vα region of the TCR (P22) that binds to WT1/HLA-A2.

SEQ ID NO:3 is the amino acid sequence of a modified Vβ region of the TCR (D13.1.1) that binds with high-affinity to WT1/HLA-A2.

SEQ ID NO:4 is the amino acid sequence of a modified Vα region of the TCR (D13.1.1) that binds with high-affinity to WT1/HLA-A2.

SEQ ID NO:5 is the amino acid sequence of a single-chain TCR (WT1-D13.1.1) that binds with high-affinity to WT1/HLA-A2.

SEQ ID NO:6 is the amino acid sequence of the WT-1 antigen.

SEQ ID NO:7 is the amino acid sequence of the Tax antigen.

SEQ ID NO:8 is the amino acid sequence of the linker.

SEQ ID NO:9 is the is the polynucleotide sequence of the primer Splice 4L.

SEQ ID NO:10 is the is the polynucleotide sequence of the reverse primer used to generate the WT1-D13 CDR1α library PreSOE #1.

SEQ ID NO:11 is the polynucleotide sequence of the forward primer used to generate the WT1-D13 CDR1α library PreSOE #2.

SEQ ID NO:12 is the is the polynucleotide sequence of the primer T7.

SEQ ID NO:13 is the is the polynucleotide sequence of the reverse primer used to generate the PreSOE #1 of the WT1-D13.1 CDR3 β1 library SEQ ID NO:14 is the is the polynucleotide sequence of the forward primer used to generate the PreSOE #2 of the WT1-D13.1 CDR3 β1 library SEQ ID NO:15 is the polynucleotide sequence of the reverse primer used to generate the PreSOE #1 of the WT1-D13.1 CDR3 β2 library.

SEQ ID NO:16 is the is the polynucleotide sequence of the forward primer used to generate the PreSOE #2 of the WT1-D13.1 CDR3 β2 library.

SEQ ID NO:17 is the polynucleotide sequence of the reverse primer used to generate the PreSOE #1 of the WT1-D13.1 CDR3α1 library SEQ ID NO:18 is the is the polynucleotide sequence of the forward primer used to generate the PreSOE #2 of the WT1-D13.1 CDR3α1 library SEQ ID NO:19 is the is the polynucleotide sequence of the reverse primer used to generate the PreSOE #1 of the WT1-D13.1 CDR3α2 library SEQ ID NO:20 is the is the polynucleotide sequence of the forward primer used to generate the PreSOE #2 of the WT1-D13.1 CDR3α2 library.

SEQ ID NO:21 is the amino acid sequence of a modified Vβ region of the TCR (D13) that binds with high-affinity to WT1/HLA-A2.

SEQ ID NO:22 is the amino acid sequence of a modified Vα region of the TCR (D13) that binds with high-affinity to WT1/HLA-A2.

SEQ ID NO:23 is the amino acid sequence of an influenza A peptide.

SEQ ID NO:24 is the amino acid sequence of a variant influenza A peptide.

SEQ ID NOs:25-34 are the amino acid sequences of ten WT1 variant peptides.

DETAILED DESCRIPTION

The following description is intended to facilitate understanding of the disclosure but is not intended to be limiting.

In general, the terms and phrases used herein have their art-recognized meaning, which can be found by reference to standard texts, journal references and contexts known to those skilled in the art. The following definitions are provided to clarify their specific use in the context of the disclosure.

As used herein, "linked" refers to an association between two groups, which can be a covalent or non-covalent association. Groups may be linked using a variable length peptide chain, a non-amino acid chemical group or other means as known in the art. A linker region can be an amino acid sequence that operably links two functional or structural domains of a protein or peptide.

As used herein, the term "chemotherapeutic agent" refers to any substance capable of reducing or preventing the growth, proliferation, or spread of a cancer cell, a population of cancer cells, tumor, or other malignant tissue. The term is intended also to encompass any antitumor or anticancer agent.

As used herein, the term "effective amount" is intended to encompass contexts such as a pharmaceutically effective amount or therapeutically effective amount. For example, in certain embodiments, the effective amount is capable of achieving a beneficial state, beneficial outcome, functional activity in a screening assay, or improvement of a clinical condition.

As used herein, the term "cancer cell" is intended to encompass definitions as broadly understood in the art. In one embodiment, the term refers to an abnormally regulated cell that can contribute to a clinical condition of cancer in a human or animal. In one embodiment, the term can refer to a cultured cell line or a cell within or derived from a human or animal body. A cancer cell can be of a wide variety of differentiated cell, tissue, or organ types as is understood in the art. Particular examples of cancer cells include breast cancer, colon cancer, skin cancer, ovarian cancer, leukemia, lung cancer, liver cancer, testicular cancer, esophageal cancer, and other types of cancer.

As used herein, "treating" or "treatment" refers to an approach for obtaining beneficial or desired results, including and preferably clinical results. Treatment can refer to either the amelioration of symptoms of the disease or condition, or the delaying of the progression of the disease or condition.

As used herein, "prevention" or "preventing" refers to an approach for preventing, inhibiting, or reducing the likelihood of, the onset or recurrence of a disease or condition. It also refers to preventing, inhibiting, or reducing the likelihood of, the occurrence or recurrence of the symptoms of a disease or condition, and it also includes reducing the intensity, effect, symptoms and/or burden of a disease or condition prior to onset or recurrence of the disease or condition.

As used herein, "inhibiting cell growth" or "inhibiting proliferation of cells" refers to reducing or halting the growth rate of cells. For example, by inhibiting the growth of tumor cells, the rate of increase in size of the tumor may slow. In other embodiments, the tumor may stay the same size or decrease in size, i.e., regress. In particular embodiments, the rate of cell growth or cell proliferation is inhibited by at least 20%, at least 30%, at least 40%, at least 50%, at least 60%, at least 70%, at least 80%, or at least 90%.

The terms "wild type" and "wt" are used interchangeably herein and are used in reference to a TCR having an amino acid sequence or a polynucleotide encoding the variable regions isolated from a naturally occurring or non-modified TCR, e.g., the original or parent T cell clone, with specificity for the antigen.

In the figures and tables that present amino acid sequences, the wild type is sometimes designated "wt". In the sequences presented below the top sequence, a dash indicates the amino acid is the same as that present in the wt or top sequence of the alignment. A letter indicates a substitution has been made in that position from the top sequence.

As used herein, the terms "modified", "variant", "mutant", "mutated" and "derived" T cell receptor refer to TCR sequences of the variable regions having one or more mutations compared to the original or wild type T cell clone. Examples of modified TCRs include higher affinity TCRs.

A coding sequence is the part of a gene or cDNA which codes for the amino acid sequence of a protein, or for a functional RNA such as a tRNA or rRNA.

Complement or complementary sequence means a sequence of nucleotides that forms a hydrogen-bonded duplex with another sequence of nucleotides according to Watson-Crick base-pairing rules.

Downstream refers to a relative position in DNA or RNA and is the region toward the 3' end of a strand.

Expression refers to the transcription of a gene into structural RNA (rRNA, tRNA) or messenger RNA (mRNA) and subsequent translation of an mRNA into a protein.

Two nucleic acid sequences are heterologous to one another if the sequences are derived from separate organisms, whether or not such organisms are of different species, as long as the sequences do not naturally occur together in the same arrangement in the same organism.

Homology refers to the extent of identity between two nucleotide or amino acid sequences.

An amino acid sequence that is functionally equivalent to a specifically exemplified TCR sequence is an amino acid sequence that has been modified by single or multiple amino acid substitutions, by addition and/or deletion of amino acids, or where one or more amino acids have been chemically modified, but which nevertheless retains the binding specificity and high affinity binding activity of a cell bound or a soluble TCR protein of the present disclosure. Functionally equivalent nucleotide sequences are those that encode polypeptides having substantially the same biological activity as a specifically exemplified cell-bound or soluble TCR protein. In the context of the present disclosure, a soluble TCR protein lacks the portions of a native cell-bound TCR and is stable in solution (i.e., it does not generally aggregate in solution when handled as described herein and under standard conditions for protein solutions).

The term "isolated" refers to a composition, compound, substance, or molecule altered by the hand of man from the natural state. For example, a composition or substance that occurs in nature is isolated if it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein.

A nucleic acid construct is a nucleic acid molecule which is isolated from a naturally occurring gene or which has been modified to contain segments of nucleic acid which are combined and juxtaposed in a manner which would not otherwise exist in nature.

Nucleic acid molecule means a single- or double-stranded linear polynucleotide containing either deoxyribonucleotides or ribonucleotides that are linked by 3'-5'-phosphodiester bonds.

Two DNA sequences are operably linked if the nature of the linkage does not interfere with the ability of the sequences to affect their normal functions relative to each other. For instance, a promoter region would be operably linked to a coding sequence if the promoter were capable of effecting transcription of that coding sequence.

A polypeptide is a linear polymer of amino acids that are linked by peptide bonds.

The term "promoter" refers to a cis-acting DNA sequence, generally 80-120 base pairs long and located upstream of the initiation site of a gene, to which RNA polymerase may bind and initiate correct transcription. There can be associated additional transcription regulatory sequences which provide on/off regulation of transcription and/or which enhance (increase) expression of the downstream coding sequence.

A recombinant nucleic acid molecule, for instance a recombinant DNA molecule, is a novel nucleic acid sequence formed in vitro through the ligation of two or more nonhomologous DNA molecules (for example a recombinant plasmid containing one or more inserts of foreign DNA cloned into at least one cloning site).

The terms "transformation" and "transfection" refer to the directed modification of the genome of a cell by the external application of purified recombinant DNA from another cell of different genotype, leading to its uptake and integration into the subject cell's genome. In bacteria, the recombinant DNA is not typically integrated into the bacterial chromosome, but instead replicates autonomously as a plasmid. The terms "transformed" and "transfected" are used interchangeably herein. For example, a T cell may be transfected with a DNA sequence encoding a modified or high affinity TCR described herein prior to adoptive T cell treatment.

Upstream means on the 5' side of any site in DNA or RNA.

A vector is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g., promoter) for the expression of the inserted DNA. Common vectors include plasmid vectors and phage vectors.

A high affinity T cell receptor (TCR) is an engineered TCR with stronger binding to a target ligand than the wild type TCR. Some examples of high affinity include an equilibrium binding constant for a target ligand of between about $10^{-6}$ M and $10^{-12}$ M and all individual values and ranges therein. This range encompasses affinities between those reported to be wild type affinities ($10^{-4}$ to $10^{-6}$ M), and those which have been isolated by directed evolution (about $10^{-12}$ M).

A cytokine is a protein, peptide or glycoprotein made by cells that affect other cells.

Mammal includes both human and non-human mammals.

It will be appreciated by those of skill in the art that, due to the degeneracy of the genetic code, numerous functionally equivalent nucleotide sequences encode the same amino acid sequence.

T Cell Receptors

The T cell receptor (TCR) is composed of two chains ($\alpha\beta$ or $\gamma\delta$) that pair on the surface of the T cell to form a heterodimeric receptor. The $\alpha\beta$ TCR is expressed on most T cells in the body and is known to be involved in the recognition of MHC-restricted antigens. The molecular genetics, structure, and biochemistry of $\alpha\beta$ TCRs have now been studied thoroughly. Each $\alpha$ and $\beta$ chain is composed of two domains: Constant domains (C) that anchor the protein in the cell membrane and that associate with invariant subunits of the CD3 signaling apparatus, and Variable domains (V) that confer antigen recognition through six loops, called complementarity determining regions (CDR). Each of the V domains has three CDRs. These CDRs interact with a complex between an antigenic peptide bound to a protein encoded by the major histocompatibility complex (pepMHC) (Davis and Bjorkman (1988) Nature, 334, 395-402; Davis et al. (1998) Annu Rev Immunol, 16, 523-544; Murphy (2012), xix, 868 p.).

Figure 5:
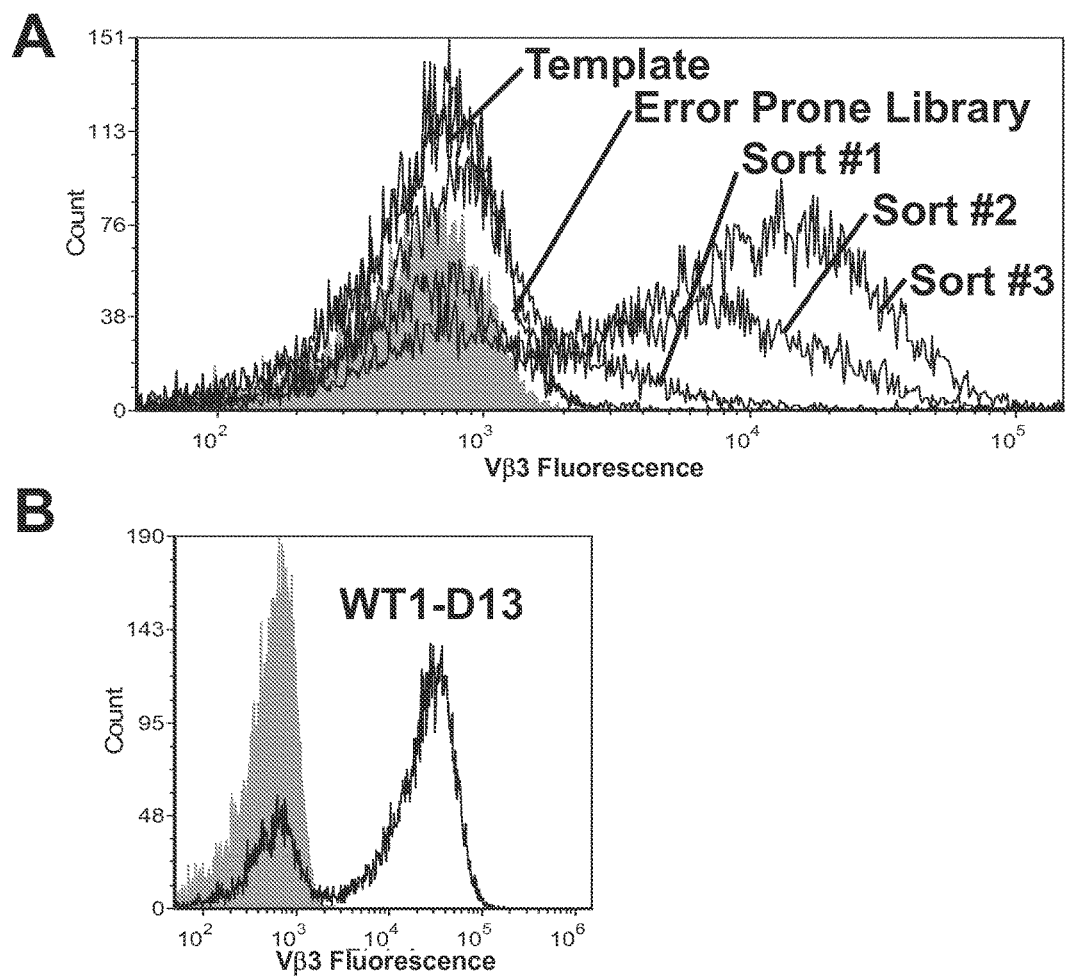
FIGS. 5A and 5B show the flow cytometry histograms of the WT1 single-chain TCR error prone library after sorting with two antibodies which recognize conformation epitopes on Vβ3. The WT1 error prone library was sorted sequentially with a 1:10 dilution of both Therma hVb3.1 FITC IgG and BC hVb3.2 FITC IgM antibodies, AlexaFluor 647 Goat anti-mouse IgG and Goat anti-mouse IgM APC, for a total of 3 sorts. Aliquots of yeast cells after each sort were then incubated with a 1:10 dilution of Therma hVb3.1 FITC IgG, AlexaFluor 647 Goat anti-mouse IgG. Gray indicates yeast cells stained with secondary antibody only (FIG. 5A). The stable clone WT1 D13, isolated after the $3^{rd}$ sort, is stained with a 1:10 dilution of Therma hVb3.1 FITC IgG, AlexaFluor 647 Goat anti-mouse IgG (FIG. 5B).

The molecular genetics of the TCR have revealed a process of genetic recombination between multiple genes that combine to form the coding region of the V domains. The process is analogous to antibody development in which the heavy and light chain genes rearrange to generate the tremendous diversity exhibited by B cell-derived antibodies (Tonegawa (1988) In Vitro Cell Dev Biol, 24, 253-65). In the case of T cells, the $\alpha$ chain V domain is formed by the rearrangement of one V region (among about 75 in humans) to one Joining (J) gene segment (among about 61 in humans) (FIG. 5.8, Janeway, 8th edition). The $\beta$ chain V domain is formed by the rearrangement of one V region (among about 52 in humans) to one Diversity (D) gene (among 2 in humans) to one Joining (J) gene segment (among 13 in humans) (FIG. 5.8, (Murphy (2012), xix, 868 p.)). The junctions of the VαJα and VβDβJβ gene rearrangements encode the CDR3 loops of each chain, and they contribute to the tremendous diversity of the αβ TCR, with a theoretical limit of over $10^{15}$ different TCRs (Davis and Bjorkman (1988) Nature, 334, 395-402), well above the achievable diversity in a human because there are only about 1011 T cells total (Mason (1998) Immunol Today, 19, 395-404). The possible CDR1 and CDR2 diversity of each chain is represented by the number of V genes, as these loops are encoded within the V gene, and TCRs do not undergo somatic mutation in vivo. Although the diversity of CDR1 and CDR2 loops are relatively limited compared to CDR3 loops, there have been a number of examples shown where there has been selection for particular V regions based on the peptide antigen and/or MHC product.

Class I MHC products bind to peptides of 8 to 10 amino acids in length and they are expressed on all nucleated cells in the body (reviewed by (Rock and Goldberg (1999) Annu Rev Immunol, 17, 739-79)). Whereas all the binding energy of an antibody-antigen interaction is focused on the foreign antigen, a substantial fraction of the binding energy of the TCR-peptide:MHC is directed at the self-MHC molecule (Manning and Kranz (1999) Immunology Today, 20, 417-422). In fact, more recent studies have suggested that particular residues of the CDR1 and/or CDR2 loops have evolved to interact with particular residues on the MHC helices, thereby providing a basal affinity for MHC, accounting for the process of MHC-restriction (Garcia et al. (2009) Nat Immunol, 10, 143-7; Marrack et al. (2008) Annu Rev Immunol, 26, 171-203).

There has been interest in using TCRs that have affinities for a peptide-MHC antigen (class I) above the normal range (so called higher affinity TCRs) in order to: 1) drive the activity of CD4 helper T cells (which lack the CD8 coreceptor) or 2) develop soluble TCRs that could be used for direct targeting of a cell, by attaching an "effector" molecule (e.g., antibody Fc regions, a toxic drug, or an antibody scFv such as an anti-CD3 antibody, to form a bispecific protein) ((Ashfield and Jakobsen (2006) Drugs, 9, 554-9; Foote and Eisen (2000) Proc Natl Acad Sci USA, 97, 10679-81; Holler et al. (2000) Proc Natl Acad Sci USA, 97, 5387-92; Molloy et al. (2005) Curr Opin Pharmacol, 5, 438-43; Richman and Kranz (2007) Biomol Eng, 24, 361-73). This approach also could overcome a problem faced by some cancer patients, whereby their T cells do not express TCRs with adequate specificity and binding affinity to potential tumor antigens (in part due to the thymic and peripheral processes of tolerance). For example, over 300 MHC-restricted, T cell-defined tumor antigens have now been identified (cancer-immunity.org/peptide/)(Boon and Old (1997) Curr Opin Immunol, 9, 681-3; Cheever et al. (2009) Clin Cancer Res, 15, 5323-37). These tumor antigens include mutated peptides, differentiation antigens, and overexpressed antigens, all of which could serve as targets for therapies. Because the majority of the cancer antigens described to date were derived from intracellular proteins that can only be targeted at the cell surface in the context of an MHC molecule, TCRs make the ideal candidate for therapeutics as they have evolved to recognize this class of antigen.

Similarly, TCRs can detect peptides derived from viral proteins that have been naturally processed in infected cells and displayed by an MHC molecule on the cell surface. Many viral antigen targets have been identified over the past 25 years, including peptides derived from viral genomes in HIV and HTLV (e.g., Addo et al. (2007) PLoS ONE, 2, e321; Tsomides et al. (1994) J Exp Med, 180, 1283-93; Utz et al. (1996) J Virol, 70, 843-51). However, patients with these diseases may lack the optimal TCRs for binding and destruction of the infected cells. Finally, it is possible that TCRs could be used as receptor antagonists of autoimmune targets, or as delivery agents to immunosuppress the local immune cell response, in a process that would be highly specific, thereby avoiding general immune suppression ((Molloy et al. (2005) Curr Opin Pharmacol, 5, 438-43; Stone et al. (2012) Protein Engineering)).

Modified T Cell Receptors

Directed evolution has been used to generate TCRs with higher affinity for a specific pepMHC. The three different display methods that have been used are yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), and T cell display (Chervin et al. (2008) J Immunol Methods, 339, 175-84). In all three approaches, the process involves the engineering of a TCR that exhibits the normal, low affinity of the wild-type TCR, so mutants of the TCR had increased affinity for the specific pepMHC (i.e., for the original antigen that the T cells were specific for). Thus, the wild-type TCR was used as a template for producing mutagenized libraries in one or more of the CDRs, followed by selection of mutants with higher affinity, by binding to the cognate peptide-MHC antigen. It is well known in the art that such in vitro, directed evolution, is necessary in order to engineer affinities that are more than just a few fold above the wild type affinity.

Yeast display allows for the protein of interest to be expressed on the surface as an Aga2-fusion (Boder and Wittrup (1997) Nat. Biotech., 15, 553-557; Boder and Wittrup (2000) Methods Enzymol, 328, 430-44). This system has been used successfully in the engineering of higher affinity TCRs, single-chain antibodies, fibronectin, and other proteins. In the yeast display system, the TCR has been displayed as a stabilized single-chain protein, in Vβ-linker-Vα or Vα-linker-Vβ forms (Aggen et al. (2011) Protein Engineering, Design, & Selection, 24, 361-72; Holler et al. (2000) Proc Natl Acad Sci USA, 97, 5387-92; Kieke et al. (1999) Proc Natl Acad Sci USA, 96, 5651-6; Richman et al. (2009) Mol Immunol, 46, 902-16; Weber et al. (2005) Proc Natl Acad Sci USA, 102, 19033-8), or as a two-chain heterodimer (Aggen et al. (2011) Protein Engineering, Design, & Selection, 24, 361-72; Richman et al. (2009) Mol Immunol, 46, 902-16). Two mouse TCRs have been engineered for higher affinity using this system: 2C (MHC class-I restricted) and 3.L2 (MHC class-II restricted) (Holler et al. (2000) Proc Natl Acad Sci USA, 97, 5387-92; Weber et al. (2005) Proc Natl Acad Sci USA, 102, 19033-8). Human TCR single-chain VαVβ fragments (called scTv or scTCR) have also recently been developed by taking advantage of the exceptional stability of the human Vα region called Vα2, also known as TCRA12 by IMGT nomenclature (Aggen et al. (2011) Protein Engineering, Design, & Selection, 24, 361-72). In this case, in vitro engineered, high-affinity T cell receptors in a single-chain format were used to isolate human stabilized scTv fragments (Vβ-linker-Vα), which could be expressed as stable proteins, both on the surface of yeast and in soluble form from E. coli. The TCRs included two stabilized, human scTv fragments, the A6 scTv that is specific for a peptide derived from the human T cell lymphotrophic virus Tax protein and the 868 scTv that is specific for a peptide derived from the human immunodeficiency virus Gag protein (peptide: SL977-85). Both of these TCRs used the Vα2 gene (IMGT: TRAV12 family), but they had CDR3α, CDR1β, CDR2β, and CDR3β residues derived from the original T cell clone from which the TCRs were isolated. Thus, the higher affinity mutants of these scTCRs were each derived from their original (parental) TCR against their cognate peptide-MHC antigens.

In a second system, phage display, the protein of interest is fused to the N-terminus of a viral coat protein (Scott and Smith (1990) Science, 249, 386-90). Various TCRs, including those called A6, 868, and 1G4 (MHC class-I restricted), have been engineered for higher affinity using this method (Li et al. (2005) Nat Biotechnol, 23, 349-54; Sami et al. (2007) Protein Eng Des Sel, 20, 397-403; Varela-Rohena et al. (2008) Nat Med, 14, 1390-5). Phage display of these TCRs was enabled by introduction of a non-native disulfide bond between the two C domains in order to promote pairing of the α and β chains. This system thus uses full-length (VαCα/VβCβ) heterodimeric proteins derived from the original T cell clones for engineering against their cognate peptide-MHC.

A third system that has been reported for the engineering of TCRs is mammalian cell display (Chervin et al. (2008) J Immunol Methods, 339, 175-84; Kessels et al. (2000) Proc Natl Acad Sci USA, 97, 14578-83). This system uses a retroviral vector to introduce the TCR α and β-chains into a TCR-negative T cell hybridoma. In one study (Kessels et al. (2000) Proc Natl Acad Sci USA, 97, 14578-83), the selected mutant TCR was shown to bind to a peptide that was structurally very similar to the cognate peptide (ASNENMDAM versus ASNENME™; SEQ ID NOs:23 and 24, respectively). In the other study, the affinity of the mutant TCR was shown to be increased for the cognate pepMHC (Chervin et al. (2008) J Immunol Methods, 339, 175-84). It has been shown in many studies that such higher affinity TCRs also exhibit higher affinities against structurally similar variants of the cognate peptide (e.g., (Holler et al. (2003) Nat Immunol, 4, 55-62)). In the mammalian cell display system, introduced TCRs were expressed on the surface in its native conformation, in complex with CD3 subunits, allowing for a fully functional T cell (signaling competent). Full-length, heterodimeric TCRs in their native host were thus engineered using this method.

High-Affinity TCRs that Bind to WT1/HLA-A2

The present invention provides for a wild type TCR and various high-affinity TCRs against the well-known cancer antigen WT1/HLA-A2. In certain embodiments, the engineered TCRs can be used in soluble form for targeted delivery in vivo, or as recombinantly expressed by T cells in an adoptive transfer method or treatment. In a particular embodiment, a single-chain VαVβ form of the TCR (scTCR) scaffold can be prepared and used with a payload such as a cytokine, toxin, radioisotope, chemotherapeutic agent, or drug (similar to antibody-drug conjugates) to deliver the effector molecule to the location where the TCR binds (e.g., tumor). The TCR can also be used in cell therapies, such as adoptive transfer of CD4+ T cells, CD8+ T cells, and/or natural killer (NK) cells, to mediate a response against cancer cells that express WT1. The scTCR scaffolds provided herein can also be used for diagnosis of, e.g., malignant or viral-infected cells through identification of, e.g., neoplastic or viral-associated cell-surface antigens by covalent linkage, for example through amine-reactive or sulfhydryl-reactive amino acid side chains of the TCR, to a detectable group, such as a radioisotope or fluorescent moiety.

In one embodiment, the scTCR proteins described herein are displayable on the surface of yeast, phage, or mammalian cells and can be used to engineer TCRs with even higher affinity to the WT1 antigen. In one embodiment, the scTCR proteins described herein can be expressed in a prokaryotic cell, such as Escherichia coli, Aspergillus niger, Aspergillus ficuum, Aspergillus awamori, Aspergillus oryzae, Trichoderma reesei, Mucor miehei, Kluyveromyces lactis, Pichia pastoris, Saccharomyces cerevisiae, Bacillus subtilis or Bacillus licheniformis, insect cells (e.g., Drosophila melanogaster), mammalian cells including cell lines such as Chinese hamster ovary cell lines (CHO), or plant species (e.g., canola, soybean, corn, potato, barley, rye, wheat) for example, or other art-known protein expression sources and produced in large quantities. The TCR can also be used, for example and by way of example only, to detect the specific peptide/MHC on the surface of a cell. In one embodiment, the scTCR genes disclosed can be linked by use of suitable peptide sequences, encoded within the DNA construct, to the genes for signaling domains and introduced into T cells that can eliminate the targeted cells. These constructs have been termed chimeric antigen receptors (CARs), which are now widely used in the field, including the use of CARs that contain a scTCR.

In the single-chain VαVβ TCR proteins provided, the variable alpha and variable beta chains are connected using any suitable peptide linker, including those known in the art such as with antibody single-chain Fv linkages (Bird et al. (1988) Science, 242, 423-426; Holliger et al. (1993) Proc Natl Acad Sci USA, 90, 6444-8; Hoogenboom (2005) Nat Biotechnol, 23, 1105-16; Turner et al. (1997) J Immunol Methods, 205, 43-54). In one embodiment, a soluble human single-chain TCR having the structure: Vα-L-Vβ or Vβ-L-Vα, wherein L is a linker peptide that links Vβ with Vα, Vβ is a TCR variable β region, and Vα is a TCR variable α region is provided.

In one embodiment, the VβVα TCR is called WT1 D13.1.1 where Vβ is a TCR variable β region of group 3, and Vα2 is a TCR variable α region of group 2 (Utz, U., et al., 1996)(Aggen, D. A., et al., 2011).

In one embodiment, the linker peptide contains more than 5 lysine residues. In one embodiment, the linker peptide contains between 5 and 30 amino acids. In one embodiment, the linker peptide has an amino acid sequence of GSADDAKKDAAKKDGKS (SEQ ID NO:8). In one embodiment, the sc VβVα TCR provided does not contain a constant region. When the terminology sc VβVα TCR is used herein, it is understood that sc VβVα TCR is also included as the terminology is understood and used in the art. Thus, the Vβ and Vα chains can be connected to each other in any configuration through the linker.

In an aspect of the disclosure, the VβVα TCR of the disclosure binds specifically to a ligand with an equilibrium binding constant $K_D$ of between about $10^{-6}$ M and $10^{-12}$ M. In one embodiment of this aspect of the disclosure, the ligand is a peptide/MHC ligand. In one embodiment, the VβVα TCR of the disclosure has enhanced affinity toward a ligand compared to the affinities of normal, wild type TCRs.

Biologically Active Groups

Also provided are VβVα TCR proteins as described herein which includes a biologically active group. As used herein, "biologically active group" is a group that causes a measurable or detectable effect in a biological system. In one embodiment, the biologically active group is selected from: an anti-tumor agent such as, but not limited to, angiogenesis inhibitors, enzyme inhibitors, microtubule inhibitors, DNA intercalators or cross-linkers, DNA synthesis inhibitors; a cytokine such as, but not limited to IL-2, IL-15, GM-CSF, IL-12, TNF-α, IFN-γ or LT-α (Schrama et al. (2006) Nat Rev Drug Discov, 5, 147-59; Wong et al. (2011) Protein Eng Des Sel, 24, 373-83); an anti-inflammatory group such as, but not limited to, TGF-β, IL-37, IL-10 (Nold et al. (2010) Nat Immunol, 11, 1014-22; Stone et al. (2012) Protein Engineering), a radioisotope such as, but not limited to, $^{90}Y$ or $^{131}I$ (Reichert and Valge-Archer (2007) Nat Rev Drug Discov, 6, 349-56); a toxin such as, but not limited to, *Pseudomonas* exotoxin A, diphtheria toxin, or the A chain of ricin (Pastan et al. (2006) Nat Rev Cancer, 6, 559-65; Schrama et al. (2006) Nat Rev Drug Discov, 5, 147-59); a drug, or an antibody such as a single-chain Fv.

In one embodiment of this aspect of the disclosure, the biologically active group is a cytotoxic molecule, sometimes referred to as a drug (e.g., in the term "antibody drug conjugate"). As used herein, "cytotoxic" means toxic to cells. Examples of cytotoxic molecules include, but are not limited to, doxorubicin, methotrexate, mitomycin, 5-fluorouracil, duocarmycin, auristatins, maytansines, calicheamicins and analogs of the above molecules (Jarvis (2012) Chemical and Engineering News, 90, 12-18; Litvak-Greenfeld and Benhar (2012) Adv Drug Deliv Rev; Ricart and Tolcher (2007) Nat Clin Pract Oncol, 4, 245-55). Cytotoxic molecules do not need to cause complete cell death, but rather, a measurable or detectable inhibition of growth or decrease in cell activity.

In one embodiment, a TCR described herein is linked to an enzyme capable of converting a prodrug into a drug. This is useful, for example, by allowing the active form of the drug to be created at the location targeted by the TCR (e.g., at the site of a tumor).

In one embodiment, the biologically active group is bound to the single-chain TCR through a linker, which may be accomplished through standard chemical reactions such as with free amine groups or sulfhydryl groups of the TCR.

In another embodiment, the TCR is attached to a single-chain antibody fragment (scFv) to generate a bispecific agent. Bispecific antibodies that contain one scFv against a tumor antigen, and one against the CD3 molecule of the T cell have now been used successfully in the clinic (Bargou et al. (2008) Science, 321, 974-7). In addition, a bispecific agent containing a TCR and a scFv against CD3 has also been reported (Liddy et al. (2012) Nat Med, 18, 980-7).

Also provided is a single-chain VβVα TCR as described herein which includes a detectable group. In one embodiment, the detectable group is one that can be detected by spectroscopic or enzyme-based methods. In one embodiment, the detectable group is a fluorescent group, such as, but not limited to fluorescein, R-phycoerythrin (PE), PE-Cy5, PE-Cy7, Texas red, or allophycocyanin (APC); a radiolabeled group such as, but not limited to, 125I, 32P, 99mTc; an absorbing group, or an enzyme with properties that generate detectable products such as, but not limited to, horseradish peroxidase, or alkaline phosphatase.

As known in the art, a biologically active group, detectable group or other group attached to the TCR can be attached using a flexible peptide linker or by chemical conjugation, and can be covalently or noncovalently attached to the TCR.

Also provided herein is a human TCR for use in a method of treating or preventing cancer in a mammal, comprising administering an effective amount of a modified TCR linked to a therapeutically effective molecule to a mammal. In a particular embodiment, the mammal is human. In another embodiment, the mammal is a companion animal (e.g., a dog, cat, rabbit, rodent, horse) or a livestock animal (e.g., a cow, horse, pig).

Also provided is an isolated single-chain TCR (scTCR) as described herein, and a method for producing the single-chain TCR in *E. coli*. Also provided is a pharmaceutical composition comprising a scTCR as described herein and a pharmaceutically acceptable carrier.

Also provided is the sc VαVβ TCRs described herein which have been linked to signaling domains that yields an active TCR on the surface of a T cell. In one embodiment, this scTCR can be used in a method of treating cancer in a mammal, comprising: cloning the TCR into a vector, introducing the vector into T cells of a patient, and adoptive transferring of the T cells back into a patient.

Modified TCR Polypeptides and Polynucleotides

The disclosure contemplates a DNA vector that includes at least one DNA segment encoding a single-chain T cell receptor (scTCR).

Those of skill in the art, through standard mutagenesis techniques, conjunction with the assays described herein, can obtain altered TCR sequences and test them for particular binding affinity and/or specificity. Useful mutagenesis techniques known in the art include, without limitation, de novo gene synthesis, oligonucleotide-directed mutagenesis, region-specific mutagenesis, linker-scanning mutagenesis, and site-directed mutagenesis by PCR (see e.g., Sambrook et al. (1989) and Ausubel et al. (1999)).

In obtaining modified TCR coding sequences, those of ordinary skill in the art will recognize that TCR-derived proteins may be modified by certain amino acid substitutions, additions, deletions, and post-translational modifications, without loss or reduction of biological activity. In particular, it is well known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

In one embodiment, a scTCR of the disclosure may contain additional mutations in any region or regions of the variable domain that results in a stabilized protein. In one embodiment, one or more additional mutations is in one or more of CDR1, CDR2, HV4, CDR3, FR2, and FR3. The regions used for mutagenesis can be determined by directed evolution, where crystal structures or molecular models are used to generate regions of the TCR which interact with the ligand of interest (antigen, for example). In other examples, the variable region can be reshaped, by adding or deleting amino acids to engineer a desired interaction between the scTCR and the ligand.

Polypeptides of the invention include modified TCRs, and antigen binding fragments thereof (e.g., scTCR), and chimeric antigen receptors (CARs). The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the modified TCRs, or antigen-binding fragments thereof, of the present disclosure, or sequences that have deletions from, additions to, and/or substitutions of one or more amino acid of a modified TCR, or antigen binding fragment thereof. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In particular embodiments, a subject modified TCR may have: a) a TCR alpha chain variable region having an amino acid sequence that is at least 80% identical, at least 85% identical, at least 90%, at least 95% or at least 98% or 99% identical, to the alpha chain variable region of a modified TCR described herein; and b) a beta chain variable region having an amino acid sequence that is at least 80% identical, at least 85%, at least 90%, at least 95% or at least 98% or 99% identical, to the beta chain variable region of a modified TCR described herein.

In particular embodiments, the modified TCR may comprise: a) a TCR alpha chain variable region comprising: i. a CDR1 region that is identical in amino acid sequence to the alpha chain CDR1 region of a selected TCR described herein; ii. a CDR2 region that is identical in amino acid sequence to the alpha chain CDR2 region of the selected TCR; and iii. a CDR3 region that is identical in amino acid sequence to the alpha chain CDR3 region of the selected TCR; and b) a beta chain variable region comprising: i. a CDR1 region that is identical in amino acid sequence to the beta chain CDR1 region of the selected TCR; ii. a CDR2 region that is identical in amino acid sequence to the beta chain CDR2 region of the selected TCR; and iii. a CDR3 region that is identical in amino acid sequence to the beta chain CDR3 region of the selected TCR; wherein the TCR specifically binds a the WT1 antigen. In a further embodiment, the modified TCR, or antigen-binding fragment thereof, is a variant modified TCR wherein the variant comprises an alpha chain and a beta chain identical to the selected modified TCR except for up to 8, 9, 10, 11, 12, 13, 14, 15, or more amino acid substitutions in the CDR regions of the V alpha and V beta regions. In this regard, there may be 1, 2, 3, 4, 5, 6, 7, 8, or in certain embodiments, 9, 10, 11, 12, 13, 14, 15 more amino acid substitutions in the CDR regions of the selected variant modified TCR. Substitutions may be in CDRs either in the V alpha and/or the V beta regions. (See e.g., Muller, 1998, Structure 6:1153-1167).

In one embodiment, a polynucleotide encoding a modified TCR, or an antigen-binding fragment thereof, is provided. In other related embodiments, the polynucleotide may be a variant of a polynucleotide encoding the modified TCR. Polynucleotide variants may have substantial identity to a polynucleotide sequence encoding a modified TCR described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence such as a sequence encoding an TCR described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the TCR encoded by the variant polynucleotide is not substantially diminished relative to an TCR encoded by a polynucleotide sequence specifically set forth herein.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., Unified Approach to Alignment and Phylogenes, pp. 626-645 (1990); Methods in Enzymology vol. 183, Academic Press, Inc., San Diego, Calif.; Higgins, D. G. and Sharp, P. M., CABIOS 5:151-153 (1989); Myers, E. W. and Muller W., CABIOS 4:11-17 (1988); Robinson, E. D., Comb. Theor 11:105 (1971); Santou, N. Nes, M., Mol. Biol. Evol. 4:406-425 (1987); Sneath, P. H. A. and Sokal, R. R., Numerical Taxonomy—the Principles and Practice of Numerical Taxonomy, Freeman Press, San Francisco, Calif. (1973); Wilbur, W. J. and Lipman, D. J., Proc. Natl. Acad., Sci. USA 80:726-730 (1983).

Alternatively, optimal alignment of sequences for comparison may be conducted by the local identity algorithm of Smith and Waterman, Add. APL. Math 2:482 (1981), by the identity alignment algorithm of Needleman and Wunsch, J. Mol. Biol. 48:443 (1970), by the search for similarity methods of Pearson and Lipman, Proc. Natl. Acad. Sci. USA 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., Nucl. Acids Res. 25:3389-3402 (1977), and Altschul et al., J. Mol. Biol. 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, Proc. Natl. Acad. Sci. USA 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an TCR as described herein. Some of these polynucleotides bear minimal sequence identity to the nucleotide sequence of the native or original polynucleotide sequence that encode modified TCRs that bind to, e.g., the same antigen. Nonetheless, polynucleotides that vary due to differences in codon usage are expressly contemplated by the present disclosure. In certain embodiments, sequences that have been codon-optimized for mammalian expression are specifically contemplated.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; and Setlow and Hollaender (1979) Genetic Engineering: Principles and Methods, Vols. 1-4, Plenum Press, New York. Abbreviations and nomenclature, where employed, are deemed standard in the field and commonly used in professional journals such as those cited herein.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50° C., 6×SSC (sodium chloride/sodium citrate buffer) and 0.1% SDS (sodium dodecyl sulfate) indicate about 60-70% homology, hybridization and wash conditions of 50-65° C., 1×SSC and 0.1% SDS indicate about 82-97% homology, and hybridization and wash conditions of 52° C., 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the Internet at ncbi.nlm.nih.gov and a version of ClustalW is available at www2.ebi.ac.uk.

Industrial strains of microorganisms (e.g., *Aspergillus niger, Aspergillus ficuum, Aspergillus awamori, Aspergillus oryzae, Trichoderma reesei, Mucor miehei, Kluyveromyces lactis, Pichia pastoris, Saccharomyces cerevisiae, Escherichia coli, Bacillus subtilis* or *Bacillus licheniformis*), insect (*Drosophila*), mammalian (e.g., Chinese hamster ovary cell lines, CHO), or plant species (e.g., canola, soybean, corn, potato, barley, rye, wheat) may be used as host cells for the recombinant production of the TCR proteins. In certain embodiments, the first step in the heterologous expression of a high affinity TCR protein or soluble protein, an expression construct is assembled to include the TCR or soluble TCR coding sequence and control sequences such as promoters, enhancers and terminators. Other sequences such as signal sequences and selectable markers may also be included. To achieve extracellular expression of the TCR, the expression construct may include a secretory signal sequence. In embodiments, the signal sequence is not included on the expression construct if cytoplasmic expression is desired. In embodiments, the promoter and signal sequence are functional in the host cell and provide for expression and secretion of the TCR or soluble TCR protein. Transcriptional terminators may be included to ensure efficient transcription. Ancillary sequences enhancing expression or protein purification may also be included in the expression construct.

Various promoters (transcriptional initiation regulatory region) may be used according to the disclosure. The selection of the appropriate promoter may be dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the disclosure. A signal sequence which is homologous to the TCR coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1000 by on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His—*S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 µg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art (λZAP and pBLUESCRIPT SK-1, Stratagene, LaJolla, Calif.; pET, Novagen Inc., Madison, Wis.—cited in Ausubel et al., 1999) and the particular choice is not critical to the disclosure. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into *S. cerevisiae* cells by protoplast transformation or electroporation. Electroporation of *S. cerevisiae* is readily accomplished, and yields transformation efficiencies comparable to spheroplast transformation.

Monoclonal or polyclonal antibodies, preferably monoclonal, specifically reacting with a TCR protein at a site other than the ligand binding site may be made by methods known in the art, and many are commercially available. See, e.g., Harlow and Lane (1988) Antibodies: A Laboratory Manual, Cold Spring Harbor Laboratories; Goding (1986) Monoclonal Antibodies: Principles and Practice, 2d ed., Academic Press, New York; and Ausubel et al. (1999) Current Protocols in Molecular Biology, John Wiley & Sons, Inc., New York.

TCRs in cell-bound or soluble form which are specific for a particular target ligand are useful, for example, as diagnostic probes for screening biological samples (such as cells, tissue samples, biopsy material, bodily fluids and the like) or for detecting the presence of the target ligand in a test sample. Frequently, the TCRs are labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. Additionally the TCR can be coupled to a ligand for a second binding molecule: for example, the TCR can be biotinylated. Detection of the TCR bound to a target cell or molecule can then be effected by binding of a detectable streptavidin (a streptavidin to which a fluorescent, radioactive, chemiluminescent, or other detectable molecule is attached or to which an enzyme for which there is a chromophoric substrate available). United States Patents describing the use of such labels and/or toxic compounds to be covalently bound to the scTCR include but are not limited to U.S. Pat. Nos. 3,817,837; 3,850,752; 3,927,193; 3,939, 350; 3,996,345; 4,277,437; 4,275,149; 4,331,647; 4,348, 376; 4,361,544; 4,468,457; 4,444,744; 4,640,561; 4,366,241; RE 35,500; 5,299,253; 5,101,827; 5,059,413.

Labeled TCRs can be detected using a monitoring device or method appropriate to the label used. Fluorescence microscopy or fluorescence activated cell sorting can be used where the label is a fluorescent moiety, and where the label is a radionuclide, gamma counting, autoradiography or liquid scintillation counting, for example, can be used with the proviso that the method is appropriate to the sample being analyzed and the radionuclide used. In addition, there can be secondary detection molecules or particle employed where there is a detectable molecule or particle which recognized the portion of the TCR which is not part of the binding site for the target ligand in the absence of a MHC component as noted herein. The art knows useful compounds for diagnostic imaging in situ; see, e.g., U.S. Pat. Nos. 5,101,827; 5,059,413. Radionuclides useful for therapy and/or imaging in vivo include $^{111}$Indium, $^{97}$Rubidium, $^{125}$Iodine, $^{131}$Iodine, $^{123}$Iodine, $^{67}$Gallium, $^{99}$Technetium. Toxins include diphtheria toxin, ricin and castor bean toxin, among others, with the proviso that once the TCR-toxin complex is bound to the cell, the toxic moiety is internalized so that it can exert its cytotoxic effect. Immunotoxin technology is well known to the art, and suitable toxic molecules include, without limitation, chemotherapeutic drugs such as vindesine, antifolates, e.g., methotrexate, cisplatin, mitomycin, anthrocyclines such as daunomycin, daunorubicin or adriamycin, and cytotoxic proteins such as ribosome inactivating proteins (e.g., diphtheria toxin, pokeweed antiviral protein, abrin, ricin, pseudomonas exotoxin A or their recombinant derivatives. See, generally, e.g., Olsnes and Pihl (1982) Pharmac. Ther. 25:355-381 and Monoclonal Antibodies for Cancer Detection and Therapy, Eds. Baldwin and Byers, pp. 159-179, Academic Press, 1985.

The general structure of TCR molecules and methods of making and using, including binding to a peptide:Major Histocompatibility Complex have been disclosed. See, for example PCT/US98/04274; PCT/US98/20263; WO99/60120. Pharmaceutical Compositions and Therapeutic Agents TCRs specific for a particular target ligand are useful in treating animals and mammals, including humans believed to be suffering from a disease associated with the particular antigen, e.g., a neoplastic disease or disorder, such as cancer. Examples of types of cancers that may be treated according to the methods described herein include, but are not limited to, Wilm's tumour, bladder cancer, breast cancer, colon cancer, colorectal cancer, esophageal carcinomas, gastric cancer, hepatocellular carcinoma, kidney cancer, leukemia, liver cancer, lung cancer, lymphoma, melanoma, neuroblastoma, non-small cell lung carcinoma, oral cancer, osteosarcoma, ovarian cancer, pancreatic cancer, prostate cancer, renal cancer, skin cancer, small cell lung carcinoma, and testicular cancer.

Therapeutic products can be made using the materials shown herein. Effective amounts of therapeutic products are the minimum dose that produces a measurable effect in a subject. Therapeutic products are easily prepared by one of ordinary skill in the art. In one embodiment, a scTCR of the disclosure is administered directly to a patient. In one embodiment, a scTCR of the disclosure is linked to PEG or to immunoglobulin constant regions, as known in the art. This embodiment lengthens the serum clearance. In one embodiment, the scTCR is linked to a chemotherapeutic agent or drug in order to deliver the drug to a target cell such as a cancer cell. In one embodiment, the scTCR is linked to a biologic effector molecule such as a cytokine (Tayal and Kalra (2008) Eur J Pharmacol, 579, 1-12). In one embodiment, the scTCR is linked to a cytokine with anti-tumor activity, such as IL-2, IL-12, or TNFα (Wong et al. (2011) Protein Eng Des Sel, 24, 373-83). In one embodiment, the scTCR is linked to an immune-inhibitory cytokine, such as IL-10 or IL-13 (Stone et al. (2012) Protein Engineering). In one embodiment, the scTCR is linked to another antigen binding molecule to form a bispecific agent (Miller et al. (2010) Protein Eng Des Sel, 23, 549-57; Thakur and Lum (2010) Curr Opin Mol Ther, 12, 340-9). In one embodiment, the bispecific molecule is comprised of a scTCR linked to a single chain Fv, such as an anti-CD3 ((Bargou et al. (2008) Science, 321, 974-7; Liddy et al. (2012) Nat Med, 18, 980-7), to crosslink T cells and diseased cells. In one embodiment, the scTCR is linked to TCR signaling domains, such as CD3, to form a chimeric antigen receptor ((Porter et al. (2011) N Engl J Med, 365, 725-33; Sadelain et al. (2009) Curr Opin Immunol, 21, 215-23; Stroncek et al. (2012) J Transl Med, 10, 48). These methods and other methods of administering, such as intravenously, are known in the art. Useful dosages can be determined by one of ordinary skill in the art.

The scTCR compositions can be formulated by any of the means known in the art. They can be typically prepared as injectables, especially for intravenous, intraperitoneal or synovial administration (with the route determined by the particular disease) or as formulations for intranasal or oral administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes.

The active ingredients are often mixed with optional pharmaceutical additives such as excipients or carriers which are pharmaceutically acceptable and compatible with the active ingredient. Suitable excipients include but are not limited to water, saline, dextrose, glycerol, ethanol, or the like and combinations thereof. The concentration of the scTCR in injectable, aerosol or nasal formulations is usually in the range of 0.05 to 5 mg/ml. The selection of the particular effective dosages is known and performed without undue experimentation by one of ordinary skill in the art. Similar dosages can be administered to other mucosal surfaces.

In addition, if desired, vaccines that could include a scTCR may contain minor amounts of pharmaceutical additives such as auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-Disoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween® 80 emulsion. Such additional formulations and modes of administration as are known in the art may also be used.

The scTCRs of the present disclosure and/or binding fragments having primary structure similar (more than 90% identity) to the TCR variable regions and which maintain the high affinity for the target ligand may be formulated into vaccines as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

scTCRs for therapeutic use are administered in a manner compatible with the dosage formulation, and in such amount and manner as are prophylactically and/or therapeutically effective, according to what is known to the art. The quantity to be administered, which is generally in the range of about 100 to 20,000 µg of protein per dose, more generally in the range of about 1000 to 10,000 µg of protein per dose. Similar compositions can be administered in similar ways using labeled scTCRs for use in imaging, for example, to detect cells to which a target ligand is bound. Precise amounts of the active ingredient required to be administered may depend on the judgment of the physician or veterinarian and may be peculiar to each individual, but such a determination is within the skill of such a practitioner.

The TCR product may be given in a single dose; two dose schedule, for example two to eight weeks apart; or a multiple dose schedule. A multiple dose schedule is one in which a primary course of treatment may include 1 to 10 or more separate doses, followed by other doses administered at subsequent time intervals as required to maintain and/or reinforce the response.

Every formulation or combination of components described or exemplified can be used to practice the disclosure, unless otherwise stated. Specific names of substances are intended to be exemplary, as it is known that one of ordinary skill in the art can name the same substances differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, target ligands, biologically active groups, starting materials, and synthetic methods other than those specifically exemplified can be employed in the practice of the disclosure without resort to undue experimentation. All art-known functional equivalents, of any such methods, target ligands, biologically active groups, starting materials, and synthetic methods are intended to be included in this disclosure. Whenever a range is given in the specification, for example, a temperature range, a time range, or a composition range, all intermediate ranges and subranges, as well as all individual values included in the ranges given are intended to be included in the disclosure.

The exact formulation, route of administration and dosage can be chosen by the individual physician in view of the patient's condition (see e.g., Fingl et. al., in The Pharmacological Basis of Therapeutics, 1975, Ch. 1 p. 1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995). Suitable routes may include, for example, oral, rectal, transdermal, vaginal, transmucosal, or intestinal administration; parenteral delivery, including intramuscular, subcutaneous, or intramedullary injections, as well as intrathecal, intravenous, or intraperitoneal injections.

For injection, the agents of the disclosure may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the disclosure into dosages suitable for systemic administration is within the scope of the disclosure. With proper choice of carrier and suitable manufacturing practice, the compositions of the present disclosure, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, and then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present disclosure include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present disclosure may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Methods of Treatment

The high affinity TCRs and pharmaceutical compositions comprising a high affinity TCR may be used, for example, to treat a patient having a cancer, tumor, malignancy, or neoplastic disease or disorder. In one embodiment, a method of treating a patient having cancer comprises administering a high affinity TCR described herein. In one embodiment, the high affinity TCR is specific for WT1. In one embodiment, the TCR comprises a Vβ comprising the amino acid sequence set forth in SEQ ID NO:3. In another embodiment, the TCR comprises a Vα comprising the amino acid sequence set forth in SEQ ID NO:4. In one embodiment, the high affinity TCR is a single chain TCR comprising the amino acid sequence set forth in SEQ ID NO:5. In another embodiment, the high affinity TCR is administered in combination with a therapeutic agent, e.g., a chemotherapeutic agent. In yet another embodiment, the high affinity TCR is conjugated to a biologically active group.

Another aspect of the invention provides a method for the adoptive transfer of T cells to a patient in need thereof, comprising administering T cells that express either the wild type TCR or a high affinity TCR described herein. In one embodiment, the T cells have been transfected with a polynucleotide that encodes a TCR that is specific for WT1. In one embodiment, the TCR comprises a Vβ comprising the amino acid sequence set forth in SEQ ID NO:3. In another embodiment, the TCR comprises a Vα comprising the amino acid sequence set forth in SEQ ID NO:4. In one embodiment, the high affinity TCR is a single chain TCR comprising the amino acid sequence set forth in SEQ ID NO:5.

EXAMPLES

The following examples further describe non-limiting examples of the disclosure.

Example 1

Engineering TCRSs for Higher Affinity for Peptide/HLA-A2 Antigens

Figure 3:
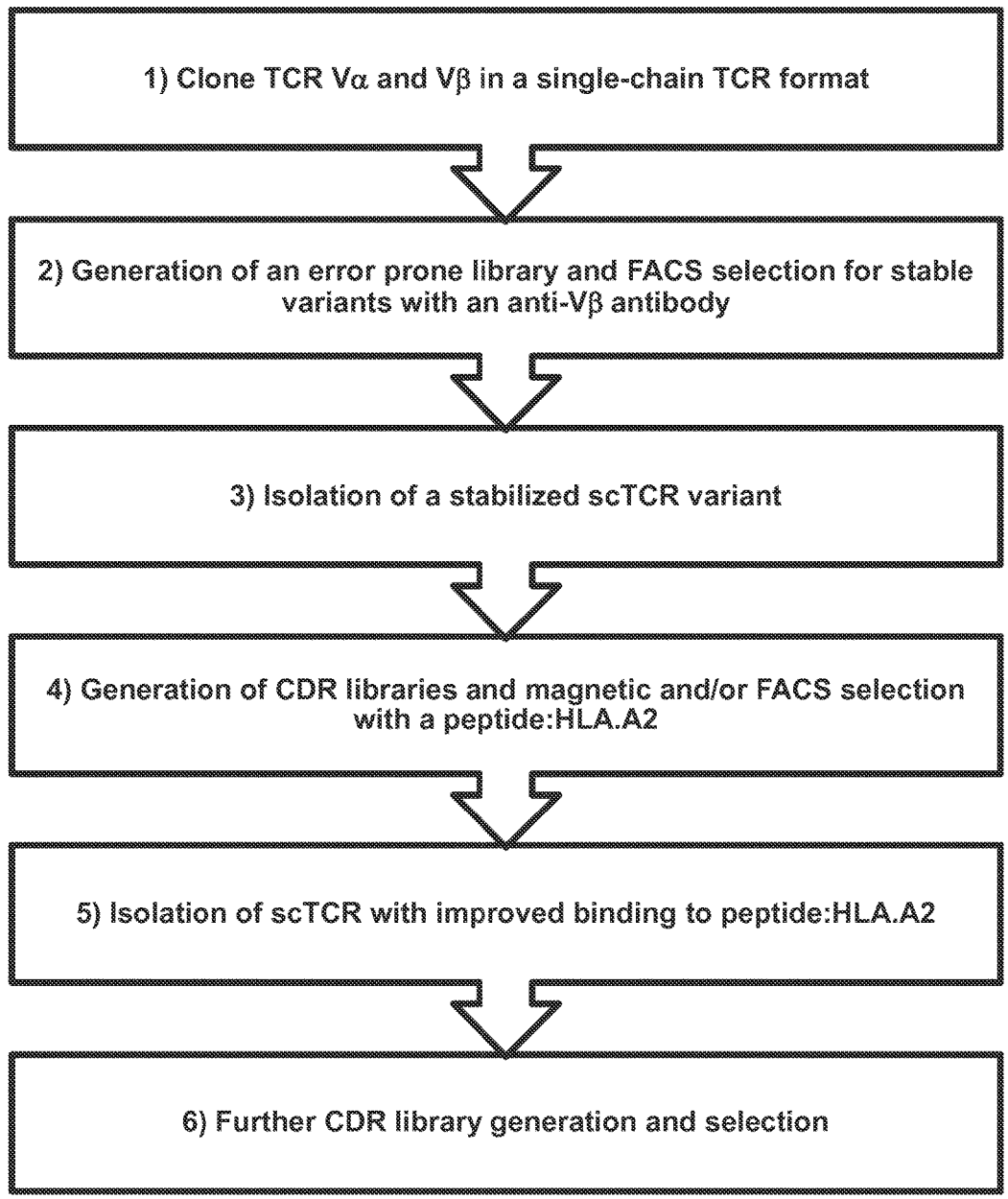
FIG. 3 is a diagram that shows a method for engineering single chain TCRs for improved affinity against a peptide:HLA.A2. The general process used to engineer high affinity TCRs is shown.
Figure 4:
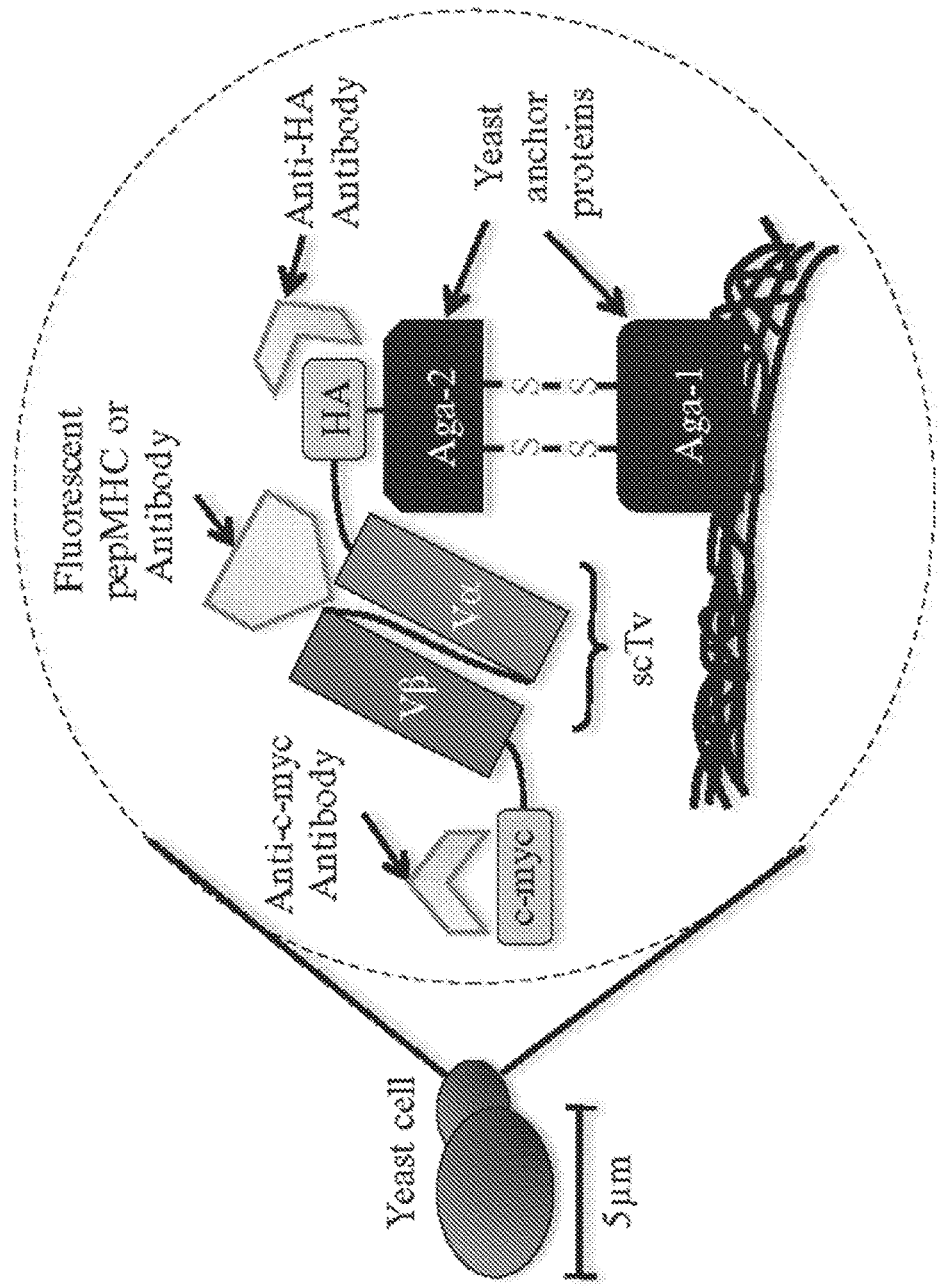
FIG. 4 is a schematic of the yeast-display system for engineering single-chain T cell receptor fragments (Vα-linker Vβ or Vβ-linker-Vα).

The general strategy used to discover, or generate single-chain TCRs for improved affinity and stability is shown in FIG. 3. The process involves six steps, as illustrated:

1) Cloning the Vα and Vβ TCR genes from a T cell clone such as P22 (sequence shown in FIG. 1, and the Vβ comprising the amino acid sequence set forth in SEQ ID NO:1 and the Vα comprising the amino acid sequence set forth in SEQ ID NO:2) as a single chain TCR format for display. The V regions recognize the HLA-A2-restricted antigenic peptide WT1 (SEQ ID NO:6) in complex with HLA-A2. In the present invention, the TCR V region genes from clone P22 (e.g. Dossett et al. (2009) Mol Ther. 17(4), 742) were cloned as a single-chain format (Vβ-linker-Vα) and introduced into a yeast display vector for expression on the surface of yeast (FIG. 4).

2) Generation of an error prone library and FACS or magnetic bead selection for stabilized variants with an anti-Vβ antibody. Because the single-chain Vα and Vβ TCRs are often unstable due to loss of the stabilizing constant regions, error-prone mutagenesis libraries are generated to select for stabilizing mutations that allow for stable expression on the surface of yeast, although other display formats including but not limited to phage and mammalian display may be used. Phage display vectors and cloning have yielded library sizes of $10^{11}$, whereas yeast display vectors and homologous recombination steps have yielded library sizes of $10^{10}$ ((Benatuil et al. (2010) Protein Eng Des Sel, 23, 155-9). Various methods have been used for selection of variants, including affinity-based binding to immobilized ligands (phage display) or magnetic particle selections with antigens (yeast display), or fluorescent activated cell sorting with labeled-peptide-MHC antigens (yeast display). Utilizing antibodies against the TCR Vβ that recognize folded epitopes, fluorescent activated cell sorting (FACS) or magnetic bead selection are used to isolate variants with improved antibody binding in the present example.

3) scTCR clones isolated from the selection of the error prone library are assessed for thermal stability and a stabilize variant is chosen for a template for affinity maturation, and sequenced. Typically, single-site mutations are identified that contribute to increased surface levels on yeast, and greater stability in solution.

4) The stabilized scTCR sequences are used as a template for the generation of CDR libraries, usually in the CDR1α, CDR3α, CDR3β, although other regions including but not limited to the CDR1β, CDR2α, CDR2β, and HV4 can also be used. In the present disclosure, yeast displayed variants are selected for improved binding to peptide:MHC, from the CDR libraries, by using magnetic bead selections and/or fluorescence activated cell sorting (FACS), although selections utilizing other methods including but not limited to panning with phage display or magnetic selections or FACS with mammalian display may be used.

5) scTCR clones isolated from the selection of the CDR libraries are assessed for specific binding to the peptide:MHC against which they were engineered. Plasmids are rescued from the yeast clones, and sequenced.

6) If further improvements of affinity required, the scTCR clone selected in step 5 can be used as a template for the generation of additional libraries in other loops or regions that did not select mutations such as CDR1α, CDR3α, CDR3β, although other regions including but not limited to the CDR1β, CDR2α, CDR2β, and HV4 can also be used. Examples of each of these steps are described further below.

Example 2

Analysis of the Human TCR A6, which Uses the Vα2, in Complex with Tax:HLA.A2

TCRs all adopt a similar Ig-fold and docking angle, and TCR recognition of pepMHC is mediated entirely by specific residues on CDR loops (Garcia et al. (2009) Nat Immunol, 10, 143-7; Marrack et al. (2008) Annu Rev Immunol, 26, 171-203; Rudolph et al. (2006) Annu Rev Immunol, 24, 419-66)). Although crystal structures for the WT1 TCRs are not available at the time of the present disclosure, the structure of the A6:Tax peptide:HLA-A2 complex (PDB: 1AO7) (Garboczi et al. (1996) Nature, 384, 134-141), which used the same Vα2 domain of the WT1 P22 TCR is shown. The side view of the complex showed that the ends of the variable domains that contained the six CDRs docked onto the Tax:HLA.A2 molecule, with the central region of the binding site positioned over the peptide Tax (FIG. 2A). The crystal structure does not include the constant region a, although the constant regions help stabilize the full length construct. Stabilizing mutations selected in step 2 described above are often selected in framework regions, such as the Vα/Vβ interface or where the junctions of the Cα/Vα or Cβ/Vβ interface occurs in the full length TCR.

The top down view of the Tax:HLA-A2 complex, with the TCR "removed", except for the six CDR loops is shown (FIG. 2B). This view shows that the TCR adopts a diagonal position over the peptide-MHC, a finding which has now been observed for all TCR:peptide-MHC structures. In this orientation, the two CDR3 loops are positioned over the peptide, while there are various residues from CDR1 and CDR2 loops that interact predominantly with the helices of the MHC molecule. For purposes of affinity maturation in steps 4 and 6, these loops are often the targeted for the generation of affinity maturations libraries, although other regions may be used.

Example 3

Yeast Display of WT1 TCRs

In order to perform selections for improved stability (step 2) or improved affinity (step 5), it is necessary to use a display system in which a library of TCR mutants can be screened for binding to an antibody which recognizes a conformation epitope or a peptide:MHC ligand, respectively. Three display systems have been used for engineering TCRs for higher affinity, and could be used for this process: yeast display, phage display, and T cell (mammalian cell) display. Alternative display methods, such as ribosome, RNA, DNA, and CIS display, may also be suitable for this process. In all of these cases, the wild type TCR with low affinity for the antigen was cloned into the system, and used as a template for engineering TCRs with enhanced stability and affinity against the peptide:MHC ligand. Any of these systems could be applied to the approach described here, in which a single TCR is used as a template for libraries and the selection of TCRs with enhanced binding properties.

In the present example, yeast display was used as the platform (FIG. 4). The WT1 TCR was used as the template for stabilizing mutations via error prone mutagenesis, and stabilized clones isolated from the selections were used as templates for affinity maturation.

Example 4

Error-Prone Library Construction and Selection of a Stabilized WT1 TCR, WT1-D13

The WT1 error-prone library was generated as previously described (Richman et al. (2009) Methods Mol Biol 504, 323-350) utilizing the WT1-reactive cell line called P22 as a template. The human WT1 error-prone scTCR library was thus introduced into the yeast display vector by combining the linearized pCT302 vector, WT1 error-prone PCR product, and competent EBY100 yeast cells. The resultant library contained about $2.3 \times 10^7$ independent clones, was judged by plating limiting dilution aliquots of yeast after electroporation. The library was selected for binding to two antibodies that recognize human hVβ3, anti-hVβ3.1 FITC IgG (Thermo Scientific) and anti-hVβ3 FITC IgM (Beckman Coulter), via FACS according to Table 1.

TABLE 1

Sorting Conditions

| Sort | Conditions |
|---|---|
| 1 | Thermo Scientific hVβ3.1 FITC (1:10); AlexaFluor ® 647 Goat anti-mouse IgG (1:100) AND Beckman Coulter hVβ3 FITC IgM (1:10); Goat anti-mouse IgM APC (1:4) |
| 2 | Thermo Scientific hVβ3.1 FITC (1:10); AlexaFluor 647 ® Goat anti-mouse IgG (1:100) AND Beckman Coulter hVβ3 FITC IgM (1:10); Goat anti-mouse IgM APC (1:4) |
| 3 | Thermo Scientific hVβ3.1 FITC (1:10); AlexaFluor ® 647 Goat anti-mouse IgG (1:100) AND Beckman Coulter hVβ3 FITC IgM (1:10); Goat anti-mouse IgM APC (1:4) |

Using thermal denaturation studies, we have identified these antibodies to recognize folded epitopes on Vβ3 (data not shown). Signals were amplified using AlexaFluor® 647 Goat anti-mouse IgG (Life Technologies) and Goat anti-mouse IgM APC (Invitrogen) secondary antibodies. During 3 iterative sorts, a Vβ3-positively staining population emerged (FIG. 5A). Following the $3^{rd}$ sort, a clone called WT1-D13 was isolated for improved Vβ3 fluorescence (FIG. 5B) and showed thermal stability when heated to 80°

C. (data not shown). The WT1-D13 clone was used as a template for affinity maturation.

Example 5

CDR1α Library Construction and Selection of a WT1 TCR with Enhanced Binding to WT1:HLA.A2, WT1.1

The stabilized WT1-D13 clone isolated from selection of error-prone PCR libraries was used as a template for generation of a CDR1α library spanning 4 adjacent residues via splicing by overlap extension (SOE)(Horton et al. (1990) Biotechniques, 8, 528-535). The human WT1-D13 CDR1α scTCR library was thus introduced into the yeast display vector by combining the linearized pCT302 vector, WT1-D13 CDR1α library PCR product, and competent EBY100 yeast cells. The resultant library contained about 3.1×10⁶ independent clones, was judged by plating limiting dilution aliquots of yeast after electroporation. The WT1-D13 CDR1α library were FACS sorted according to the Table 2 for binding to WT1 (RMFPNAPYL, SEQ ID NO:6)/HLA.A2/Ig dimers (BD DimerX).

TABLE 2

Sorting Conditions

| Sort | Conditions |
|---|---|
| 1 | 100 nM WT1:HLA.A2 dimer |
|   | APC-conjugated goat anti-mouse secondary antibody (1:100) |
| 2 | 100 nM WT1:HLA.A2 dimer |
|   | APC-conjugated goat anti-mouse secondary antibody (1:100) |
| 3 | 100 nM WT1:HLA.A2 dimer |
|   | APC-conjugated goat anti-mouse secondary antibody (1:100) |
| 4 | 100 nM WT1:HLA.A2 dimer |
|   | APC-conjugated goat anti-mouse secondary antibody (1:100) |
| 5 | 200 nM WT1:HLA.A2 dimer |
|   | APC-conjugated goat anti-mouse secondary antibody (1:100) |

Figure 6:
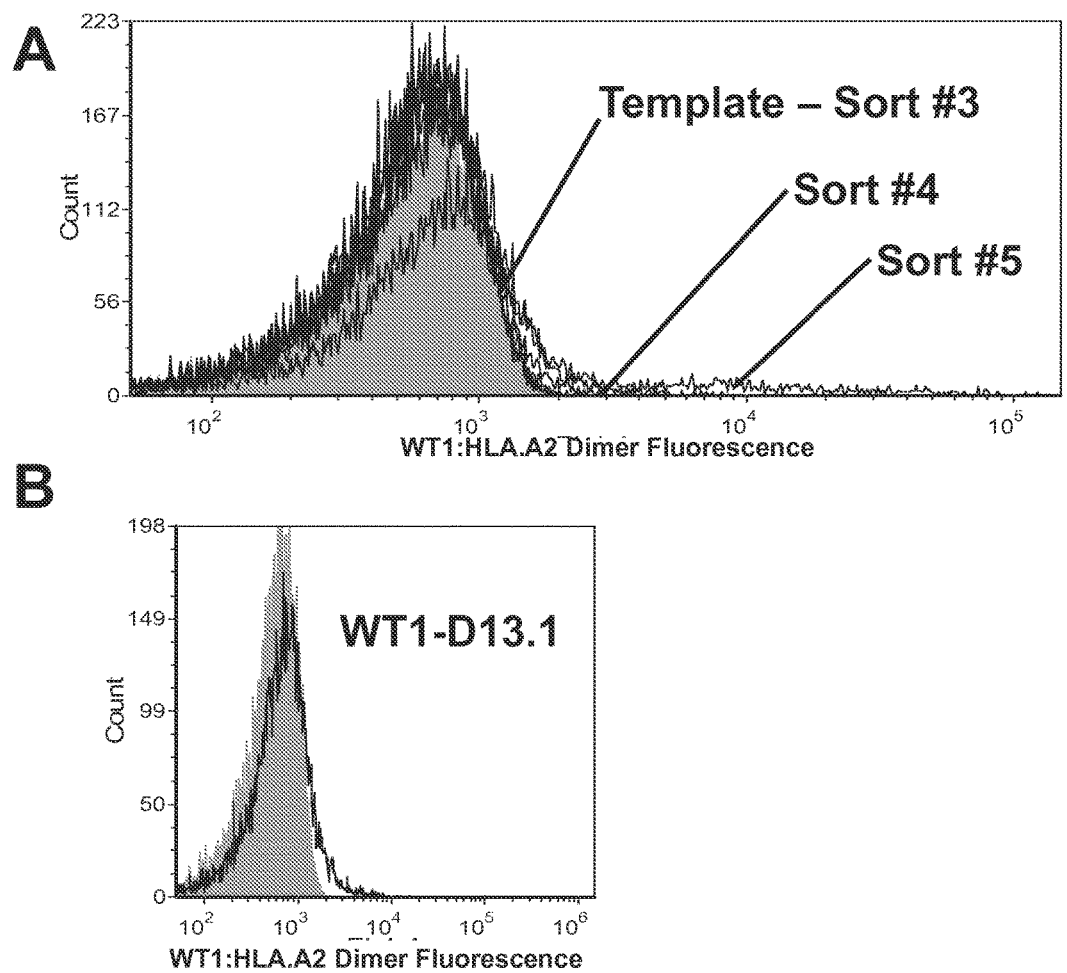
FIGS. 6A and 6B show the flow cytometry histograms of the WT1 single-chain TCR D13 CDR1α library after sorting with WT1:HLA.A2. The WT1 D13 CDR1α library was sorted sequentially with 100-200 nM WT1:HLA-A2 dimer (DimerX; obtained from BD Pharmingen), APC-conjugated goat anti-mouse secondary antibody, for a total of five sorts. Aliquots of yeast cells after each sort were then incubated with 100 nM WT1:HLA-A2 dimer (DimerX; obtained from BD Pharmingen), followed by APC-conjugated goat anti-mouse secondary antibody. Gray indicates yeast cells stained with secondary antibody only (FIG. 6A). Clone WT1 D13.1, isolated after the $5^{th}$ sort, is stained with 100 nM WT1:HLA-A2 dimer (DimerX; obtained from BD Pharmingen), followed by APC-conjugated goat anti-mouse secondary antibody (FIG. 6B).

After five rounds of selection by FACS with WT1 (RMFPNAPYL, SEQ ID NO:6)/HLA-A2/Ig dimers, a modestly positively staining population began to emerge (FIG. 6A). Clone WT1-D13.1, isolated following the 5$^{th}$ sort, showed a modest binding improvement to WT1 (RMFPNAPYL, SEQ ID NO:6)/HLA.A2 and was used as a template for further affinity maturation (FIG. 6B).

Example 6

CDR3 Library Construction and Selection of a WT1 TCR with Further Enhanced Binding to WT1:HLA.A2, WT1.1.1

In order to further improve the affinity of the WT1 scTCR, CDR3 libraries were generated using the WT1-D13.1 clone isolated from the WT1-D13 CDR1α library as a template. The WT1-D13.1 CDR3 libraries were generated by splicing by overlap extension (SOE) PCR, making degenerate codons spanning 5 adjacent codons in each CDR3 at a time (2 libraries in the CDR33 loop; 2 in the CDR3α loop). Each WT1-D13.1 CDR3 library was thus introduced into the yeast display vector by combining the linearized pCT302 vector, WT1-D13.1 CDR3 PCR product (i.e. CDR3α1, CDR3α2, CDR3β1, or CDR3β2 library), and competent EBY100 yeast cells. The four resultant libraries were pooled and the resultant combined library contained about 3.5×10⁶ independent clones as determined by plating limiting dilution aliquots of yeast after electroporation. The WT1-D13 CDR3 combined libraries were FACS sorted according to the chart in Table 3 for binding to WT1 (RMFPNAPYL, SEQ ID NO:6)/HLA.A2/Ig dimers (BD DimerX).

TABLE 3

Sorting Conditions

| Sort | Conditions |
|---|---|
| 1 | 100 nM WT1:HLA.A2 dimer |
|   | APC-conjugated goat anti-mouse secondary antibody (1:100) |
| 2 | 100 nM WT1:HLA.A2 dimer |
|   | APC-conjugated goat anti-mouse secondary antibody (1:100) |
| 3 | 10 nM WT1:HLA.A2 dimer |
|   | APC-conjugated goat anti-mouse secondary antibody (1:100) |

Figure 7:
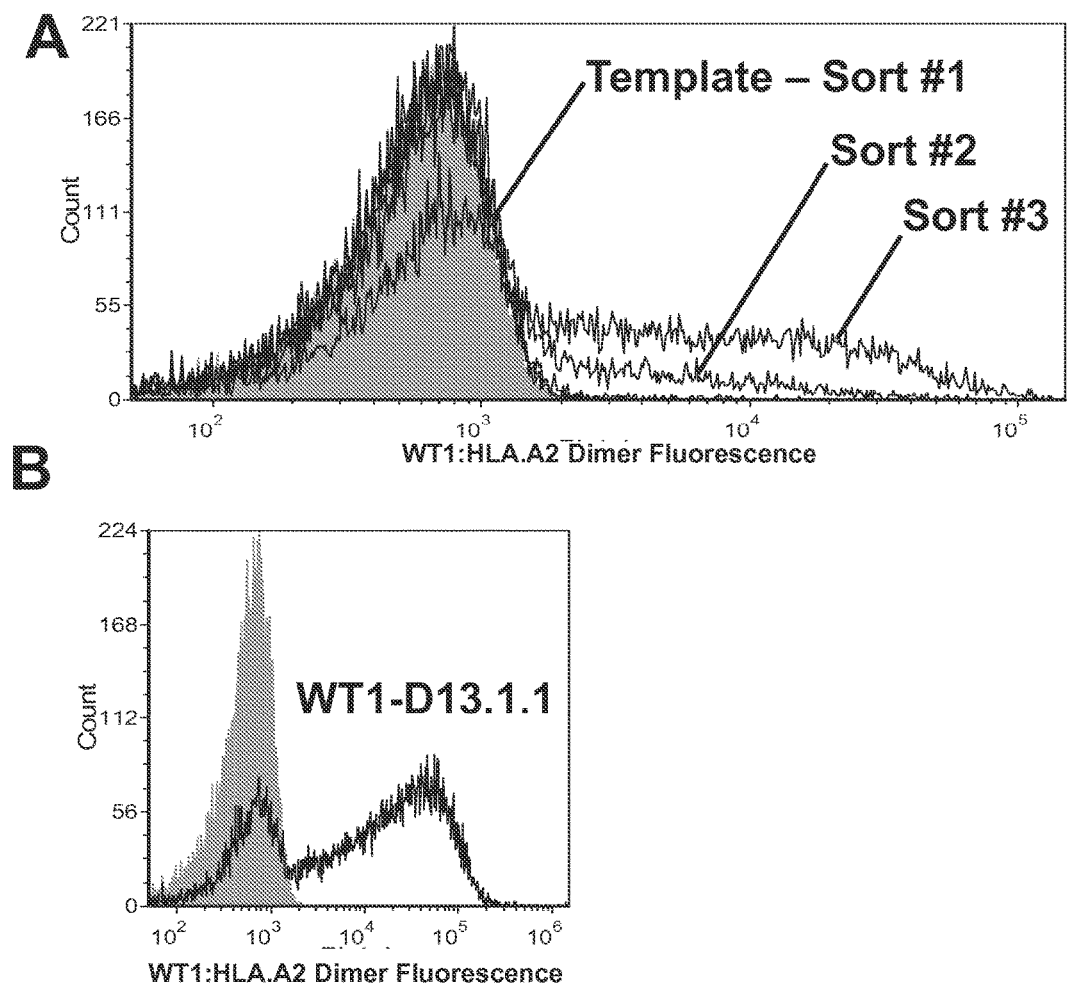
FIGS. 7A and 7B show the flow cytometry histograms of the WT1 single-chain TCR D13.1 combined CDR3 library after sorting with WT1:HLA.A2. The WT1 D13.1 combined CDR3 library was sorted sequentially with 10-100 nM WT1:HLA-A2 dimer (DimerX; obtained from BD Pharmingen), APC-conjugated goat anti-mouse secondary antibody, for a total of three sorts. Aliquots of yeast cells after each sort were then incubated with 100 nM WT1:HLA-A2 dimer (DimerX; obtained from BD Pharmingen), followed by APC-conjugated goat anti-mouse secondary antibody. Gray indicates yeast cells stained with secondary antibody only (FIG. 7A). The improved binding clone WT1 D13.1.1, isolated after the $3^{rd}$ sort, is stained with 100 nM WT1:HLA-A2 dimer (DimerX; obtained from BD Pharmingen), followed by APC-conjugated goat anti-mouse secondary antibody (FIG. 7B).

After three rounds of selection by FACS with WT1 (RMFPNAPYL, SEQ ID NO:8)/HLA-A2/Ig dimers, a positively staining population began to emerge (FIG. 7A). Clone WT1-D13.1.1, isolated following the 3$^{rd}$ sort, showed increased binding to WT1 (RMFPNAPYL, SEQ ID NO:8)/HLA.A2 (FIG. 7B).

Example 7

Binding Analysis of High Affinity WT1 TCR, WT1-D13.1.1

Figure 8:
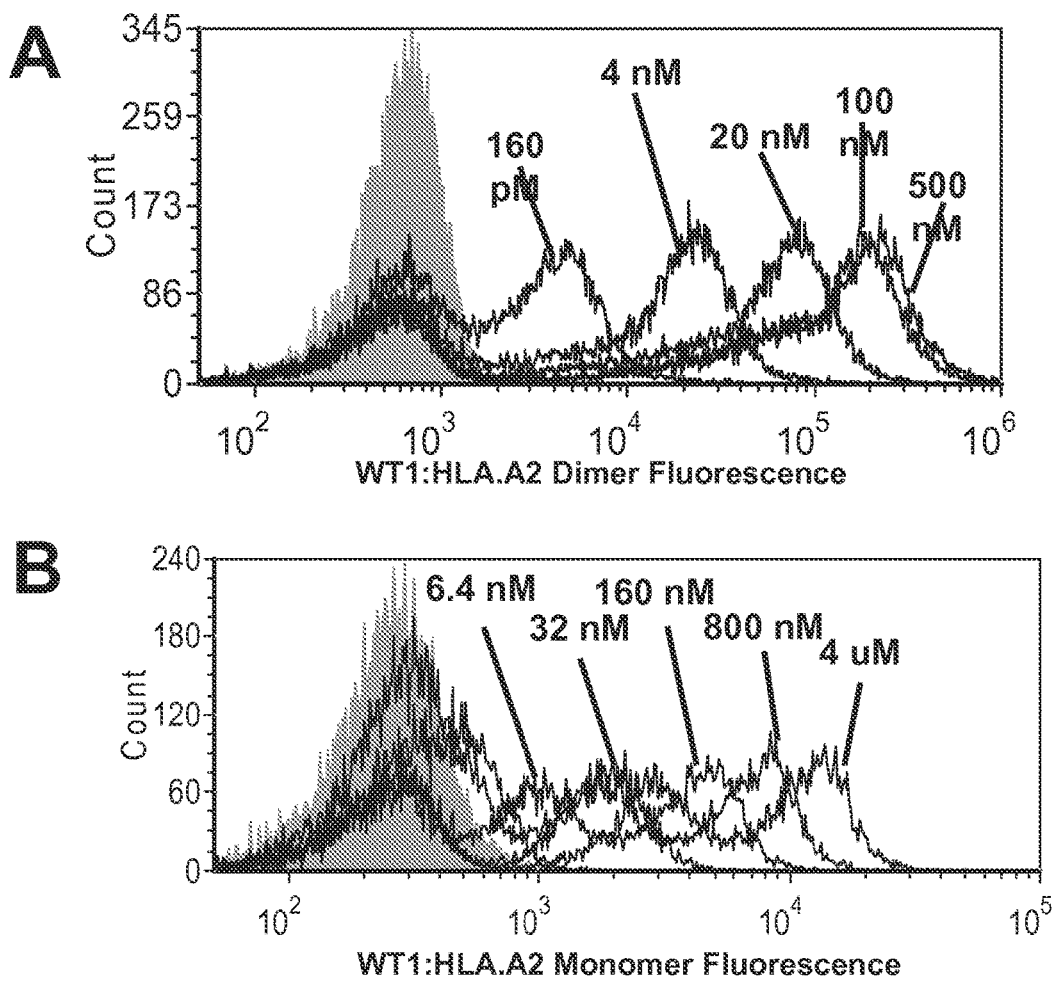
FIGS. 8A-8D show the binding properties of a high-affinity TCR, WT1 D13.1.1, for WT1:HLA-A2 dimers and monomers.
Figure 8:
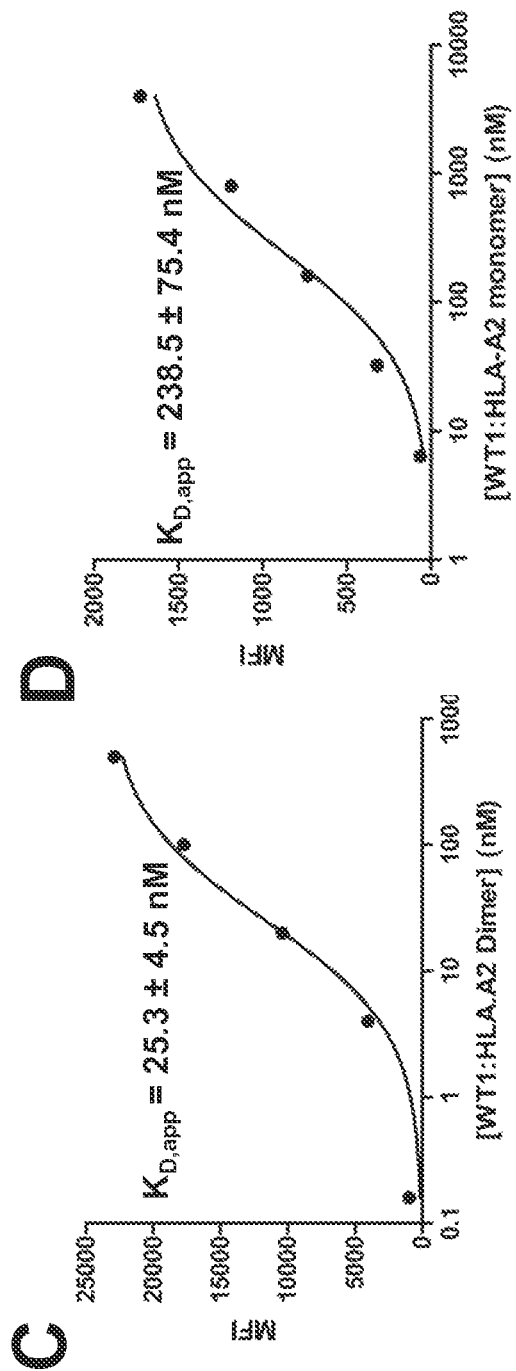

In order to assess the binding of the WT1-D13.1.1 clone isolated from selections of CDR3 libraries, yeast displaying the WT1-D13.1.1 were titrated with WT1 (RMFPNAPYL, SEQ ID NO:6)/HLA.A2 dimers HLA-A2-Ig) and monomers expressed and purified from *E. coli*. The WT-1/A2 dimers were assayed at 160 µM to 500 nM (FIG. 8A), and the monomers were assayed at 6.4 nM to 4 µM (FIG. 8B). Yeast cells were then washed and analyzed by flow cytometry. Mean fluorescence intensity (MFI) were plotted for each histogram versus the concentration of the WT-1/HLA-A2 complex. Values were normalized using nonlinear regression analysis and $K_{D,app}$ values of 25 nM and 240 nM were determined for dimmer and monomer, respectively (FIGS. 8C and 8D). Thus the WT1-D13.1.1 exhibited nanomolar affinity.

Example 8

Binding Analysis of Soluble High Affinity WT1 TCR, WT1-D13.1.1

Figure 9:
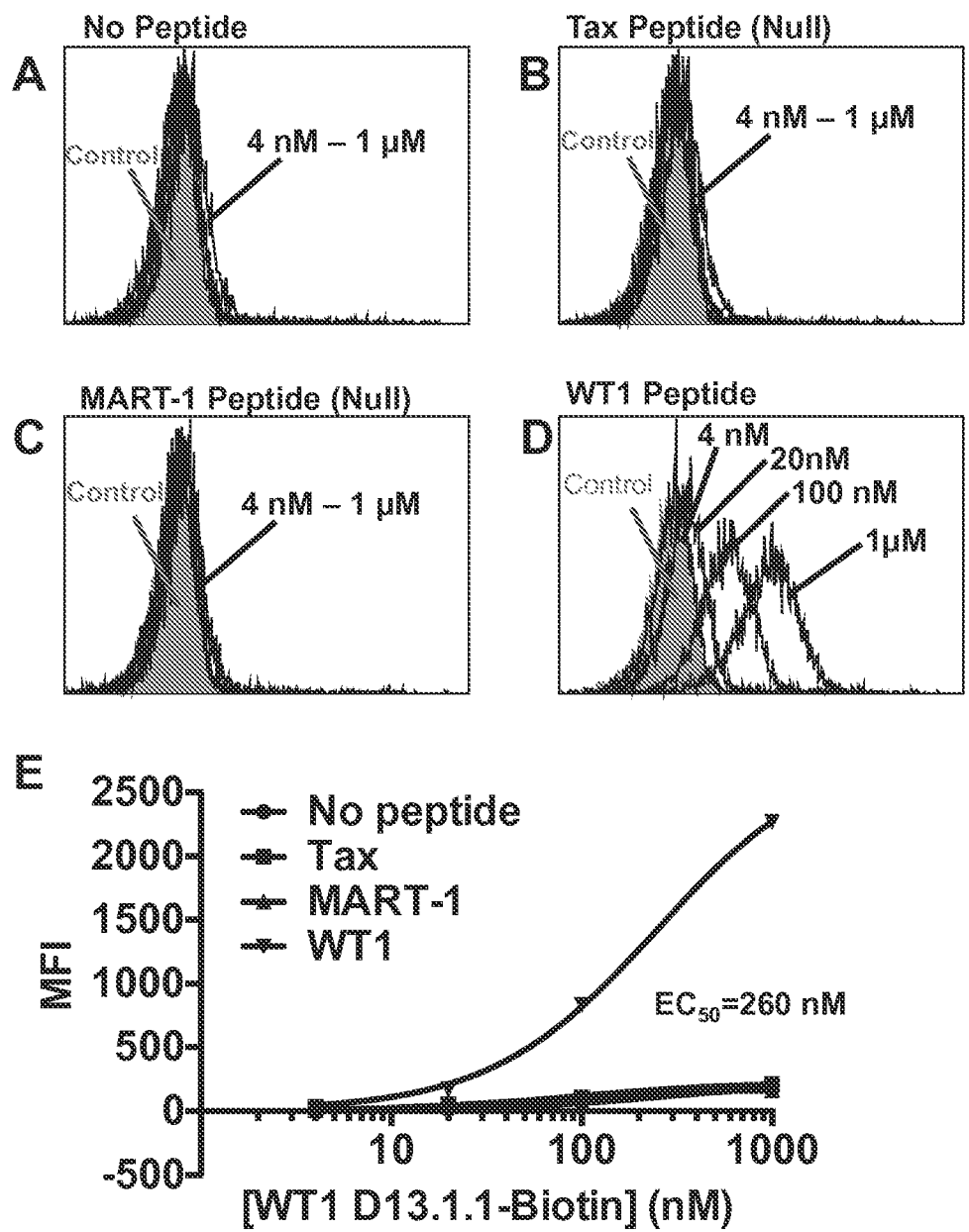
FIGS. 9A-E show the binding of soluble high-affinity TCR WT1 D13.1.1 that was expressed in *E. coli*.

To further show that the WT1-D13.1.1 scTv specifically bound WT1/HLA-A2 with high-affinity, a soluble form of WT1-D13.1.1 scTv was expressed and refolded from *E. coli* inclusion bodies and biotinylated via a C-terminal BirA tag (Aggen et al. (2011) Protein Engineering, Design, & Selection, 24, 361-72; Zhang et al. (2007) J Exp Med, 204, 49-55). The human cell line T2 (HLA-A2+) was incubated with 1 µM Tax, MART-1, or WT1 peptides and washed. Biotinylated WT1-D13.1.1 scTv was titrated on T2 cells pre-loaded without peptide (FIG. 9A), or with the negative peptide Tax (4 nM to 1 µM) (FIG. 9B), null peptide MART-1 (4 nM to 1 µM) (FIG. 9C), WT1 (4 nM to 1 µM) (FIG. 9D). The cells were washed and incubated with SA-PE and analyzed by flow cytometry. Only cells loaded with WT1 peptide were bound by the WT1-D13.1.1 TCR (FIG. 9A-D) showing that the soluble TCR was specific for WT1. Nonlinear regression of the plot of MFI versus TCR concentration of the WT1 titration showed that the soluble TCR exhibited a minimum $K_D$ value of 260 nM (FIG. 9E).

Example 9

Sequence Analysis of the Isolated TCRs for Improved Affinity Against the WT1 Antigen Sequences of the WT1-specific (P22, D13, D13.1, D13.1 and D13.1.1) single-chain TCRs were determined from isolated plasmids, and are shown in FIG. 1. The amino acid sequences of the Vβ chain of P22, D13, D13.1, D13.1 and D13.1.1 are set forth in SEQ ID NOs:1, 21, 21, 3 and 3, respectively, and the amino acid sequences of the Vα chain of P22, D13, D13.1, D13.1 and D13.1.1 are set forth in SEQ ID NOs:2, 22, 4, 2, and 4, respectively. Note that D13.1 was constructed by removing the CDR1α mutations from the final affinity matured scTCR D13.1.1 (SEQ ID NO: 5). The underlined amino acid positions in FIG. 1 indicate mutations that arose from error-prone library selections for stabilizing mutations. The amino acid positions in boxes show the affinity enhancing mutations that were selected from CDR libraries.

Example 10

Figure 10:
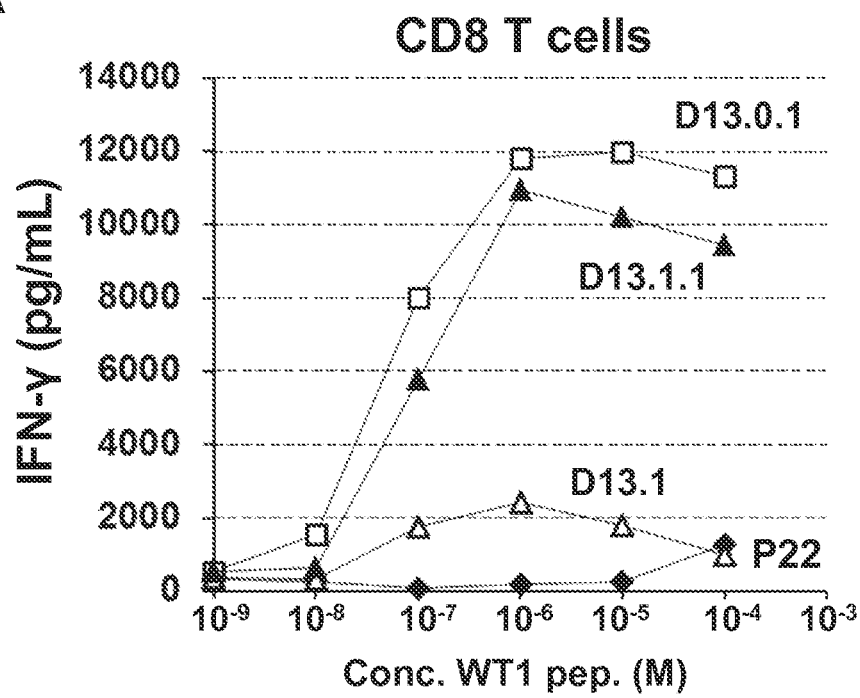
FIGS. 10A and 10B show the activity of wild-type P22, D13.1, D13.1 and D13.1.1 TCRs in mouse T cells. Isolated mouse CD8 (FIG. 10A) and CD4 (FIG. 10B) T cells were transduced with P22, D13.1, D13.1 and D13.1.1 TCRs (modified TCRs did not contain the D13 "stabilizing" mutations in the Vβ region: F48S and D51G). Transduced T cells were then incubated with HLA-A2+APCs and various concentrations of the WT1 peptide. Following 24 hours incubation, IFN-γ concentrations were measured using a standard ELISA.
Figure 10:
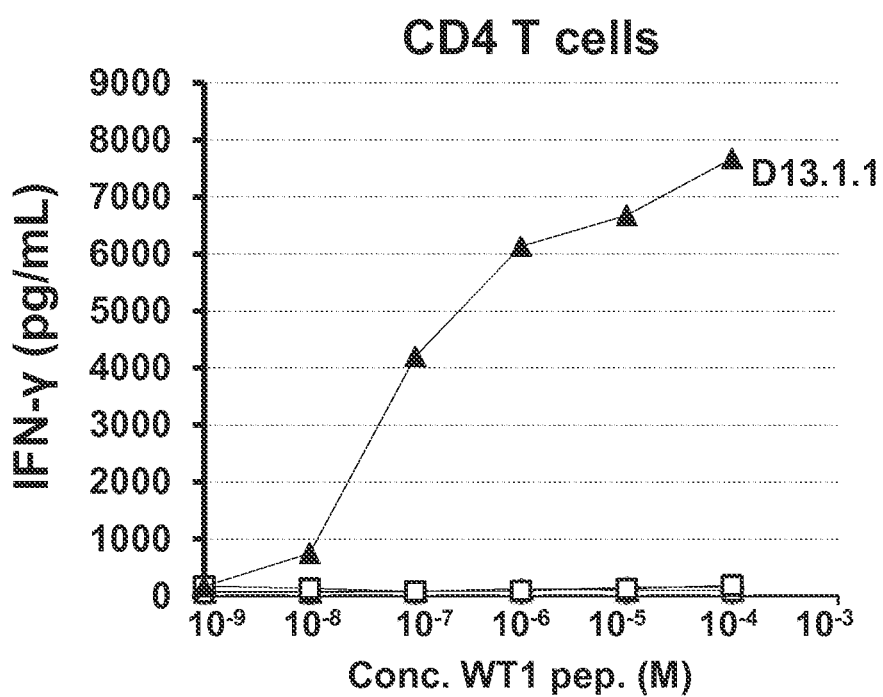

In Vitro Activity of the WT1-P22, WT1-D13.1, WT1-D13.1 and WT1-D13.1.1 TCRs in CD8 and CD4 T Cells To assess the activity of the different WT1-specific TCRs in T cells, CD8 (FIG. 10A) and CD4 (FIG. 10B) T cells were isolated from AAD transgenic mice (these are mice that have a hybrid class I gene consisting of the α1 and α2 domains of HLA-A2 and the α3 domain of the mouse $D^b$; these AAD mice are available from Jackson Laboratories). The cells were activated with beads coupled with anti-CD3 and anti-CD28 antibodies and then transduced with the WT1-P22, WT1-D13.1, WT1-D13.1 and WT1-D13.1.1 TCRs (sequences did not contain the D13 stabilizing mutations, Vβ F48S and D51 G), as described in Chervin et al, (2013) Gene Ther. 20(6):634-44. T cells were incubated with different concentrations of the peptide WT1 and AAD blast cells prepared by Concanavalin A stimulations of splenic cells from AAD mice. After a 24-hour incubation, supernatants were analyzed for IFN-γ concentration using an ELISA. CD8 T cells showed the greatest activity with the D13.1 and D13.1.1 TCRs (FIG. 10A). CD4 T cells were only activated with the D13.1.1 TCR, showing that D13.1.1 can mediate activity independently of CD8 (FIG. 10B). No reactivity has been observed with other HLA-A2 binding peptides such as MART1.

Example 11

WT1-D13.1.1 TCR in CD8 T Cells are not Reactive with Human Peptides that are Structurally Similar to WT1

Figure 11:
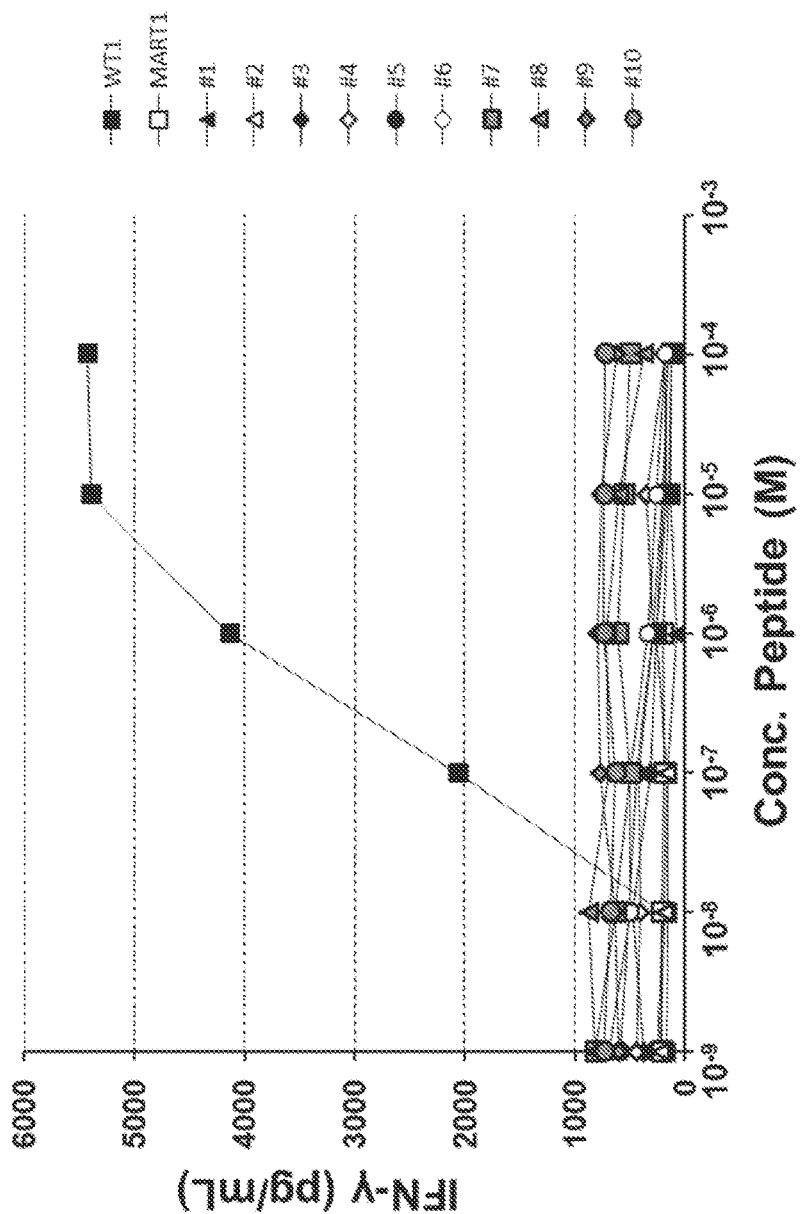
FIG. 11 shows that the high-affinity TCR WT1 D13.1.1 in CD8 T cells did not show activity against a panel of WT1 structurally similar human peptides. WT1 structurally similar peptides were determined through searches of the human proteome for peptides with conservative mutations at each of the 9 residues of the WT1 peptide (SEQ ID NO:6). The 10 peptides that were predicted to bind to HLA-A2 with highest affinity were then synthesized. Peptide numbers 1-10 correspond to SEQ ID NOs:25-34, respectively. Mouse CD8 T cells were isolated and transduced with the D13.1.1 TCR (did not contain D13 stabilizing mutations in Vβ region, F48S and D51 G) and incubated for 24 hours with respective peptides and HLA-A2+APCs.

To further determine the specificity of the high-affinity WT1-D13.1.1 TCR, in vitro activity with peptides structurally similar to the WT1 peptide was assessed. A proteome search was conducted for peptides structurally similar to the WT1 peptide, based on conservative mutations at the 9 residues of WT1. Peptides present in the human proteome were then accessed for binding ability to HLA-A2 via prediction algorithms. The ten peptides that were predicted to bind HLA-A2 with the highest affinity (FIG. 11) were synthesized and tested for ability to activated CD8 T cells transduced with the high-affinity WT1-D13.1.1 TCR. None of these peptides displayed activity, suggesting that this TCR maintains specificity when presented with these 10 structurally similar peptides.

Example 12

Therapeutic Formats of the WT1, WT1-D13.1 and WT1-D13.1.1 TCRs

Figure 12:
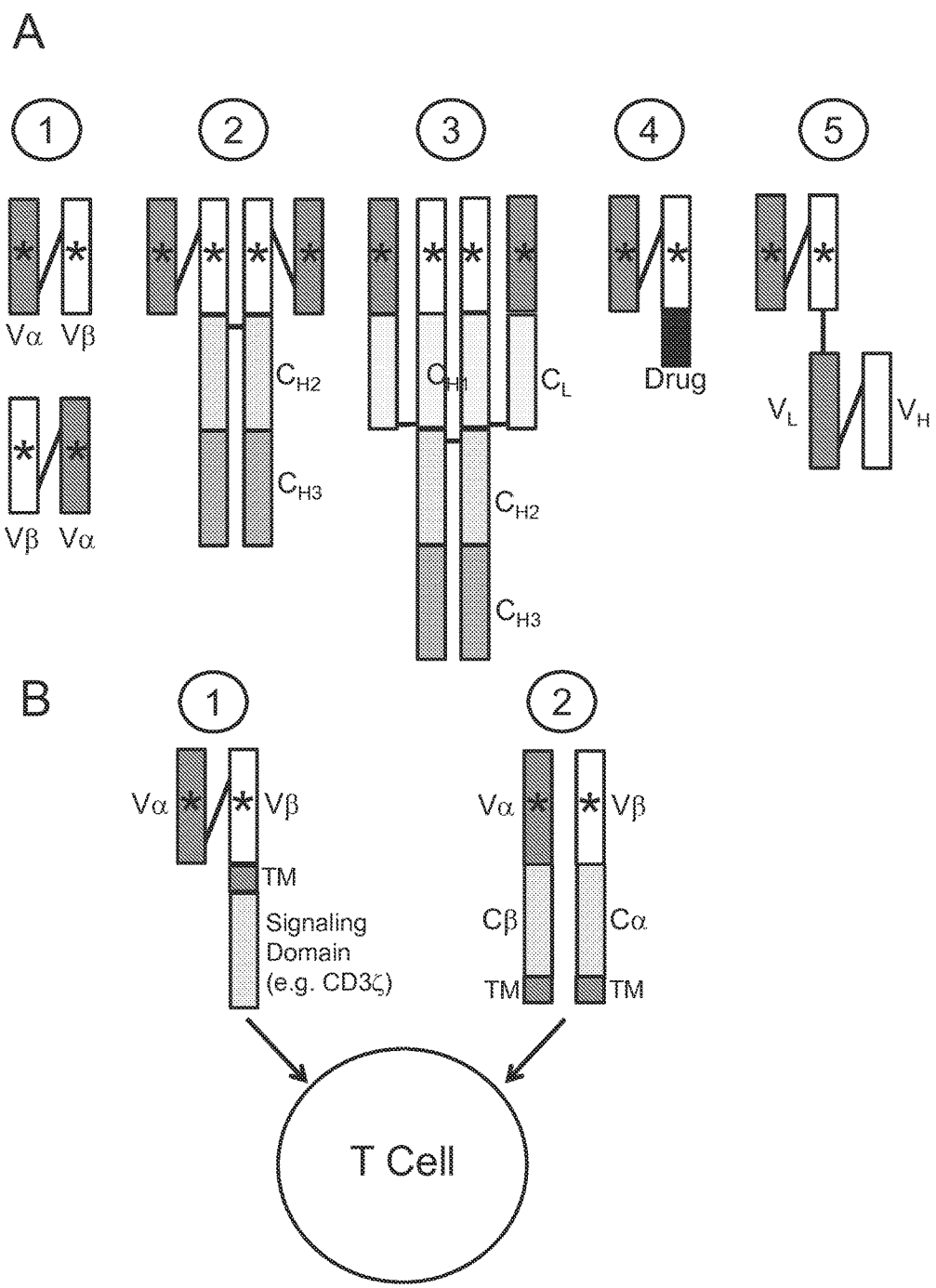
FIGS. 12A and 12B are diagrams that illustrates exemplary therapeutic applications of the WT1-specific TCRs.

It is now well known that higher affinity TCRs can be used in various formats for targeting cells that express the corresponding antigen. Thus, it is clear that the TCRs generated from the engineering strategies shown above can be used either in soluble form or in TCR gene therapy for adoptive T cell therapies, as illustrated in FIG. 12.

Materials and Methods

Antibodies, peptide:HLA-A2, MACS, and Flow Cytometry Reagents

Antibodies used to detect yeast surface expression included: anti-HA epitope tag (Clone HA.11; Covance), anti-hVβ3 FITC antibody (Clone CH92; Beckman-Coulter), anti-hVβ3.1 FITC antibody (Clone 8F10; Thermo Scientific), anti-hVβ20 antibody (Clone ELL1.4; Beckman-Coulter), anti-Vα2 monoclonal antibody generated in our laboratory (data not shown), Goat-anti-mouse IgM APC (Life Technologies), Goat-anti-mouse IgG F(ab')$_2$ AlexaFluor® 647 secondary antibody (Invitrogen), Streptavidin-phycoerythrin (SA:PE, BD Pharmingen), and MACS microbeads (Miltenyi Biotec).

Peptides that bind to HLA-A2 [WT1$_{126-134}$: RMFP-NAPYL (SEQ ID NO:6) were synthesized by standard F-moc (N-(9-fluorenyl)methoxycarbonyl) chemistry at the Macromolecular Core Facility at Penn State University College of Medicine (Hershey, Pa., USA). For FACS and flow cytometry analysis, recombinant soluble dimeric HLA-A2:Ig fusion protein (BD™ DimerX) was used. Additionally, a monomeric HLA.A2-biotin reagent generated by the exchange of a UV-cleavable peptide for another HLA.A2-restricted peptide in the presence of UV light was utilized for flow cytometry and MACS selections (Rodenko et al. (2006) Nat Protoc, 1, 1120-1132; Toebes et al. (2006) Nat Med, 12, 246-251).

Cloning and Expression of scTv in Yeast Display Vectors

TCR variable region fragments (scTv) were expressed in yeast display plasmid pCT302 (Vβ-L-Vα) (Boder and Wittrup (2000) Methods Enzymol, 328, 430-444), which contains a galactose-inducable AGA2 fusion allowing for growth in Trp media. Induction of the scTv gene involves growth of the transformed EBY100 yeast cells to stationary phase in selection media followed by transfer to galactose-containing media. The template WT1 single-chain TCR gene was synthesized by Genscript (Piscataway, N.J., USA) with a F49S mutation in the Vα2-domain of the construct (Aggen et al. (2011) Protein Eng Des Sel, 24, 361-372).

The WT1-specific TCR genes were isolated from CTL clones (TCR genes against WT1 from Phillip Greenberg; e.g. Dossett et al. (2009) Mol Ther. 17(4), 742) and the genes were synthesized by Genscript, cloned as a single-chain format (Vβ-linker-Vα), introduced into a yeast display vector for expression on the surface of yeast. The scTvs consisted of the variable contains attached by the linker region GSADDAKKDAAKKDGKS (SEQ ID NO:8) (Hoo et al. (1992) Proc Natl Acad Sci USA, 89, 4759-4763; Weber et al. (2005) Proc Natl Acad Sci USA, 102, 19033-19038;

Aggen et al. (2011) Protein Eng Des Sel, 24, 361-372). The scTv was introduced into the NheI and XhoI restrictions sites of pCT302.

Generation, Display, and Selection of Mutated scTv Yeast Display Libraries

Error-prone PCR was used to generate random mutations, as previously described (Richman et al. (2009) Mol Immunol, 46, 902-916). CDR1 and 3 libraries were generated using Splicing by overlap extension (SOE) PCR spanning 4-5 adjacent codons at a time (Horton et al. (1990) Biotechniques, 8, 528-535).

For the WT1-D13 CDR1α library, pre-SOE PCR products were generated utilizing the following primer pairs: 5'-GGC AGC CCC ATA AAC ACA CAG TAT-3' (Splice 4L) (SEQ ID NO:9) and 5'-ACG ATC GCT ATA GGT GCA GTT CAA TGA TGC AAT AGC ACC TTC CGG GAO ACT TAA TGG GCC GCT-3'(SEQ ID NO:10), and 5'-ATT GCA TCA TTG AAC TGC ACC TAT AGC GAT CGT NNS NNS NNS NNS TTC TTT TGG TAT AGA CAG TAO AGT GGC AAA TCC CCG-3' (SEQ ID NO:11) and 5'-TAA TAO GAO TCA CTA TAG GG-3' (T7) (SEQ ID NO:12). SOE PCR was performed with each corresponding Pre-SOE along with both T7 and Splice 4L.

For the WT1-D13.1 CDR3 libraries, pre-SOE PCR products were generated for each of the four libraries utilizing the following primer pairs: β1:5'-GGC AGC CCC ATA AAC ACA CAG TAT-3' (Splice 4L) (SEQ ID NO:9). and 5'-TGC ACA CAG GTA CAT GGA AGT TTG ATT GGT ACT AGC GCT TTC CAG AAT CAA ACT GAA ACG TTC TTT-3' (SEQ ID NO:13), and 5'-AGT ACC AAT CAA ACT TCC ATG TAO CTG TGT GCA NNS NNS NNS NNS NNS GAA CAG TTT TTC GGC CCA GGT ACA AGA TTA ACG GTG-3' (SEQ ID NO:14) and 5'-TAA TAO GAO TCA CTA TAG GG-3' (T7) (SEQ ID NO:12); β2: Splice 4L (SEQ ID NO:9) and 5'-TGC ACA CAG GTA CAT GGA AGT TTG ATT GGT ACT AGC GCT TTC CAG AAT CAA ACT GAA ACG TTC TTT-3' (SEQ ID NO:15), and 5'-AGT ACC AAT CAA ACT TCC ATG TAO CTG TGT GCA AGC AGT TCC ATC NNS NNS NNS NNS NNS GGC CCA GGT ACA AGA TTA ACG GTG-3' (SEQ ID NO:16) and T7 (SEQ ID NO:12); α1: Splice 4L (SEQ ID NO:9) and 5'-GGC GCA CAG GTA AGT GGC GCT ATC TGA CGG TTG GCT ATC ACG GAT TAA CAG AGA GAO ATA CTG GGA-3' (SEQ ID NO:17), and 5'-CAA CCG TCA GAT AGC GCC ACT TAO CTG TGC GCC NNS NNS NNS NNS NNS AAT ATG CTG ACC TTC GGT GGC GGT ACT CGC TTA ATG-3' (SEQ ID NO:18) and T7 (SEQ ID NO:12); α2: Splice 4L (SEQ ID NO:9) and 5'-GGC GCA CAG GTA AGT GGC GCT ATC TGA CGG TTG GCT ATC ACG GAT TAA CAG AGA GAO ATA CTG GGA-3' (SEQ ID NO:19), and 5'-CAA CCG TCA GAT AGC GCC ACT TAO CTG TGC GCC GCG AAT AAC GCG NNS NNS NNS NNS NNS TTC GGT GGC GGT ACT CGC TTA ATG-3' (SEQ ID NO:20) and T7 (SEQ ID NO:12).

Yeast libraries were made by homologous recombination in EBY100 yeast by electroporating error prone or SOE PCR products along with NheI and XhoI digested pCT302 (Horton et al. (1990) Biotechniques, 8, 528-535). The libraries were induced in galactose-containing media (SG-CAA) for 48 h, washed with 1 mL 1% PBS/BSA, and stained with antibodies or peptide:MHC reagents at the concentrations indicated in FIGS. 4A, 5A, 6A, 8A, and 9A. Cells were washed (1 ml, 1% PBS/BSA), and the most fluorescent cells were selected using a FACS Aria (BD Bioscience) high-speed sorter or via MACS LS columns on a QuadroMACS™ Separator (Miltenyl Biotec). In order to test thermal stability of isolated clones, yeast were incubated at elevated temperature for 30 min prior to the staining protocol (data not shown).

Isolation and Staining of High Affinity Clones

Following selections, library clones were isolated by plating limiting dilutions. Colonies were expanded and induced in galactose-containing media (SG-CAA) for 48 hours, washed with 1 mL 1% PBS/BSA, and stained with various concentrations of peptide/HLA.A2 DimerX, goat-anti-mouse IgG F(ab')$_2$ AlexaFluor® 647 secondary antibody, or various concentrations of UV-exchanged peptide/HLA.A2, SA-PE. Cells were washed (1 ml, 1% PBS/BSA) and analyzed on an Accuri C6 flow cytometer.

Plasmids were recovered using Zymoprep™ Yeast Plasmid Miniprep II (Zymo Research) and introduced back into *E. coli* via heat shock transformation into Subcloning Efficiency™ DH5α™ Competent Cells (Invitrogen). *E. coli* cells were expanded and plasmids were isolated using QIAprep Spin Miniprep Kit (Qiagen). Sequences of individual clones were determined by Sanger sequencing Statements Regarding Incorporation by Reference and Variations All references cited herein, for example patent documents including issued or granted patents or equivalents; patent application publications; and nonpatent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the disclosure pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art or to use methods or materials that are in the state of the art without the specific inclusion of the methods or materials in the disclosure herein. For example, when a compound is claimed, it should be understood that compounds known in the prior art, including certain compounds disclosed in the references disclosed herein (particularly in referenced patent documents), are not intended to be included in the claim.

When a Markush group or other grouping is used herein, all individual members of the group and all combinations and subcombinations possible of the group are intended to be individually included in the disclosure.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the disclosure are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive. For clarification, as used herein "comprising" is synonymous with "having," "including," "containing," or "characterized by," and is inclusive or open-ended and does not exclude additional, unrecited elements or method steps. As used herein, "consisting of" excludes any element, step, component, or ingredient not specified in the claim element. As used herein, "consisting essentially of" does not exclude materials or steps that do not materially affect the basic and novel characteristics of the claim (e.g., not affecting an active ingredient). In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

The disclosure has been described with reference to various specific and preferred embodiments and techniques. However, it should be understood that many variations and modifications may be made while remaining within the spirit and scope of the disclosure. It will be appreciated by one of ordinary skill in the art that compositions, methods, devices, device elements, materials, optional features, procedures and techniques other than those specifically described herein can be applied to the practice of the disclosure as broadly disclosed herein without resort to undue experimentation. All art-known functional equivalents of compositions, methods, devices, device elements, materials, procedures and techniques described herein; and portions thereof; are intended to be encompassed by this disclosure. Whenever a range is disclosed, all subranges and individual values are intended to be encompassed. This disclosure is not to be limited by the embodiments disclosed, including any shown in the drawings or exemplified in the specification, which are given by way of example or illustration and not of limitation. Some references provided herein are incorporated by reference herein to provide details concerning additional starting materials, additional methods of synthesis, and additional methods of analysis and additional uses of the disclosure.

One skilled in the art would readily appreciate that the present disclosure is well adapted to carry out the objects and obtain the ends and advantages mentioned, as well as those inherent therein. The compositions and methods and accessory methods described herein as presently representative of preferred embodiments are exemplary and are not intended as limitations on the scope of the disclosure. Changes therein and other uses will occur to those skilled in the art, which are encompassed within the spirit of the disclosure.

REFERENCES

1. Addo M. M., Draenert R., Rathod A., Verrill C. L., Davis B. T., Gandhi R. T., Robbins G. K., Basgoz N. O., Stone D. R., Cohen D. E., Johnston M. N., Flynn T., Wurcel A. G., Rosenberg E. S., Altfeld M. and Walker B. D. (2007) Fully Differentiated HIV-1 Specific CD8+ T Effector Cells Are More Frequently Detectable in Controlled than in Progressive HIV-1 Infection. PLoS ONE 2, e321.
2. Aggen D. H., Chervin A. S., Insaidoo F. K., Piepenbrink K., H., Baker B. M. and Kranz D. M. (2011) Identification and engineering of human variable regions that allow expression of stable single-chain T cell receptors. Protein Engineering, Design, & Selection 24, 361-72.
3. Anikeeva N., Mareeva T., Liu W. and Sykulev Y. (2009) Can oligomeric T-cell receptor be used as a tool to detect viral peptide epitopes on infected cells? Clin Immunol 130, 98-109.
4. Armstrong K. M., Piepenbrink K. H. and Baker B. M. (2008) Conformational changes and flexibility in T-cell receptor recognition of peptide-MHC complexes. Biochem J 415, 183-96.
5. Ashfield R. and Jakobsen B. K. (2006) Making high-affinity T-cell receptors: a new class of targeted therapeutics. Drugs 9, 554-9.
6. Bargou R., Leo E., Zugmaier G., Klinger M., Goebeler M., Knop S., Noppeney R., Viardot A., Hess G., Schuler M., Einsele H., Brandl C., Wolf A., Kirchinger P., Klappers P., Schmidt M., Riethmuller G., Reinhardt C., Baeuerle P. A. and Kufer P. (2008) Tumor regression in cancer patients by very low doses of a T cell-engaging antibody. Science 321, 974-7.
7. Benatuil L., Perez J. M., Belk J. and Hsieh C. M. (2010) An improved yeast transformation method for the generation of very large human antibody libraries. Protein Eng Des Sel 23, 155-9.
8. Bird R. E., Hardman K. D., Jacobson J. W., Johnson S., Kaufman B. M., Lee S. M., Lee T., Pope S. H., Riordan G. S. and Whitlow M. (1988) Single-chain antigen-binding proteins. Science 242, 423-426.
9. Boder E. T. and Wittrup K. D. (1997) Yeast surface display for screening combinatorial polypeptide libraries. Nat. Biotech. 15, 553-557.
10. Boder E. T. and Wittrup K. D. (2000) Yeast surface display for directed evolution of protein expression, affinity, and stability. Methods Enzymol 328, 430-44.
11. Boon T. and Old L. J. (1997) Cancer tumor antigens. Curr Opin Immunol 9, 681-3.
12. Borbulevych O. Y., Santhanagopolan S. M., Hossain M. and Baker B. M. (2011) TCRs used in cancer gene therapy cross-react with MART-1/Melan-A tumor antigens via distinct mechanisms. J Immunol 187, 2453-63.
13. Brower V. (1997) Enbrel's phase III reinforces prospects in RA [news]. Nat Biotechnol 15, 1240.
14. Bulek A. M., Cole D. K., Skowera A., Dolton G., Gras S., Madura F., Fuller A., Miles J. J., Gostick E., Price D. A., Drijfhout J. W., Knight R. R., Huang G. C., Lissin N., Molloy P. E., Wooldridge L., Jakobsen B. K., Rossjohn J., Peakman M., Rizkallah P. J. and Sewell A. K. (2012) Structural basis for the killing of human beta cells by CD8(+) T cells in type 1 diabetes. Nat Immunol 13, 283-9.
15. Cheever M. A., Allison J. P., Ferris A. S., Finn O. J., Hastings B. M., Hecht T. T., Mellman I., Prindiville S. A., Viner J. L., Weiner L. M. and Matrisian L. M. (2009) The prioritization of cancer antigens: a national cancer institute pilot project for the acceleration of translational research. Clin Cancer Res 15, 5323-37.
16. Chervin A. S., Aggen D. H., Raseman J. M. and Kranz D. M. (2008) Engineering higher affinity T cell receptors using a T cell display system. J Immunol Methods 339, 175-84.
17. Chervin A S, Stone J D, Soto C M, Engels B, Schreiber H, Roy E J, and Kranz D M. (2013) Design of T-cell receptor libraries with diverse binding properties to examine adoptive T-cell responses. Gene Ther. 20(6):634-44
18. Colby D. W., Kellogg B. A., Graff C. P., Yeung Y. A., Swers J. S. and Wittrup K. D. (2004) Engineering antibody affinity by yeast surface display. Methods Enzymol 388, 348-58.
19. Davis M. M. and Bjorkman P. J. (1988) T-cell antigen receptor genes and T-cell recognition. Nature 334, 395-402.
20. Davis M. M., Boniface J. J., Reich Z., Lyons D., Hampl J., Arden B. and Chien Y. (1998) Ligand recognition by alpha beta T cell receptors. Annu Rev Immunol 16, 523-544.
21. Ding Y. H., Baker B. M., Garboczi D. N., Biddison W. E. and Wiley D. C. (1999) Four Aβ-TCR/peptide/HLA- A2 structures that generate very different T cell signals are nearly identical. Immunity 11, 45-56.
22. Foote J. and Eisen H. N. (2000) Breaking the affinity ceiling for antibodies and T cell receptors. Proc Natl Acad Sci USA 97, 10679-81.
23. Garboczi D. N., Ghosh P., Utz U., Fan Q. R., Biddison W. E. and Wiley D. C. (1996) Structure of the complex between human T-cell receptor, viral peptide and HLA-A2. Nature 384, 134-141.
24. Garcia K. C., Adams J. J., Feng D. and Ely L. K. (2009) The molecular basis of TCR germline bias for MHC is surprisingly simple. Nat Immunol 10, 143-7.
25. Haidar J. N., Pierce B., Yu Y., Tong W., Li M. and Weng Z. (2009) Structure-based design of a T-cell receptor leads to nearly 100-fold improvement in binding affinity for pepMHC. Proteins 74, 948-60.
26. Harkiolaki M., Holmes S. L., Svendsen P., Gregersen J. W., Jensen L. T., McMahon R., Friese M. A., van Boxel G., Etzensperger R., Tzartos J. S., Kranc K., Sainsbury S., Harlos K., Mellins E. D., Palace J., Esiri M. M., van der Merwe P. A., Jones E. Y. and Fugger L. (2009) T cell-mediated autoimmune disease due to low-affinity cross-reactivity to common microbial peptides. Immunity 30, 348-57.
27. Hawse W. F., Champion M. M., Joyce M. V., Hellman L. M., Hossain M., Ryan V., Pierce B. G., Weng Z. and Baker B. M. (2012) Cutting edge: evidence for a dynamically driven T cell signaling mechanism. J Immunol 188, 5819-23.
28. Holler P. D., Chlewicki L. K. and Kranz D. M. (2003) TCRs with high affinity for foreign pMHC show self-reactivity. Nat Immunol 4, 55-62.
29. Holler P. D., Holman P. O., Shusta E. V., O'Herrin S., Wittrup K. D. and Kranz D. M. (2000) In vitro evolution of a T cell receptor with high affinity for peptide/MHC. Proc Natl Acad Sci USA 97, 5387-92.
30. Holliger P., Prospero T. and Winter G. (1993) "Diabodies": small bivalent and bispecific antibody fragments. Proc Natl Acad Sci USA 90, 6444-8.
31. Hoogenboom H. R. (2005) Selecting and screening recombinant antibody libraries. Nat Biotechnol 23, 1105-16.
32. Jarvis L. M. (2012) Rethinking Antibody-Drug Conjugates. Chemical and Engineering News 90, 12-18.
33. Kessels H. W., van Den Boom M. D., Spits H., Hooijberg E. and Schumacher T. N. (2000) Changing T cell specificity by retroviral T cell receptor display. Proc Natl Acad Sci USA 97, 14578-83.
34. Kieke M. C., Shusta E. V., Boder E. T., Teyton L., Wittrup K. D. and Kranz D. M. (1999) Selection of functional T cell receptor mutants from a yeast surface-display library. Proc Natl Acad Sci USA 96, 5651-6.
35. Lauck F., Smith C. A., Friedland G. F., Humphris E. L. and Kortemme T. (2010) RosettaBackrub—a web server for flexible backbone protein structure modeling and design. Nucleic Acids Res 38, W569-75.
36. Li Y., Moysey R., Molloy P. E., Vuidepot A. L., Mahon T., Baston E., Dunn S., Liddy N., Jacob J., Jakobsen B. K. and Boulter J. M. (2005) Directed evolution of human T-cell receptors with picomolar affinities by phage display. Nat Biotechnol 23, 349-54.
37. Liddy N., Bossi G., Adams K. J., Lissina A., Mahon T. M., Hassan N. J., Gavarret J., Bianchi F. C., Pumphrey N. J., Ladell K., Gostick E., Sewell A. K., Lissin N. M., Harwood N. E., Molloy P. E., Li Y., Cameron B. J., Sami M., Baston E. E., Todorov P. T., Paston S. J., Dennis R. E., Harper J. V., Dunn S. M., Ashfield R., Johnson A., McGrath Y., Plesa G., June C. H., Kalos M., Price D. A., Vuidepot A., Williams D. D., Sutton D. H. and Jakobsen B. K. (2012) Monoclonal TCR-redirected tumor cell killing. Nat Med.
38. Litvak-Greenfeld D. and Benhar I. (2012) Risks and untoward toxicities of antibody-based immunoconjugates. Adv Drug Deliv Rev.
39. Manning T. C. and Kranz D. M. (1999) Binding energetics of T-cell receptors: correlation with immunological consequences. Immunology Today 20, 417-422.
40. Marrack P., Scott-Browne J. P., Dai S., Gapin L. and Kappler J. W. (2008) Evolutionarily conserved amino acids that control TCR-MHC interaction. Annu Rev Immunol 26, 171-203.
41. Marsh S. G. E., Parham P. and Barber L. D. (2000) The HLA Facts Book. Academic Press, London.
42. Mason D. (1998) A very high level of crossreactivity is an essential feature of the T-cell receptor. Immunol Today 19, 395-404.
43. Miller B. R., Demarest S. J., Lugovskoy A., Huang F., Wu X., Snyder W. B., Croner L. J., Wang N., Amatucci A., Michaelson J. S. and Glaser S. M. (2010) Stability engineering of scFvs for the development of bispecific and multivalent antibodies. Protein Eng Des Sel 23, 549-57.
44. Molloy P. E., Sewell A. K. and Jakobsen B. K. (2005) Soluble T cell receptors: novel immunotherapies. Curr Opin Pharmacol 5, 438-43.
45. Murphy K. (2012) Janeway's immunobiology. Garland Science, New York.
46. Nold M. F., Nold-Petry C. A., Zepp J. A., Palmer B. E., Bufler P. and Dinarello C. A. (2010) IL-37 is a fundamental inhibitor of innate immunity. Nat Immunol 11, 1014-22.
47. Pastan I., Hassan R., Fitzgerald D. J. and Kreitman R. J. (2006) Immunotoxin therapy of cancer. Nat Rev Cancer 6, 559-65.
48. Pierce B. G., Haidar J. N., Yu Y. and Weng Z. (2010) Combinations of affinity-enhancing mutations in a T cell receptor reveal highly nonadditive effects within and between complementarity determining regions and chains. Biochemistry 49, 7050-9.
49. Porter D. L., Levine B. L., Kalos M., Bagg A. and June C. H. (2011) Chimeric antigen receptor-modified T cells in chronic lymphoid leukemia. N Engl J Med 365, 725-33.
50. Reichert J. M. and Valge-Archer V. E. (2007) Development trends for monoclonal antibody cancer therapeutics. Nat Rev Drug Discov 6, 349-56.
51. Ricart A. D. and Tolcher A. W. (2007) Technology insight: cytotoxic drug immunoconjugates for cancer therapy. Nat Clin Pract Oncol 4, 245-55.
52. Richman S. A., Aggen D. H., Dossett M. L., Donermeyer D. L., Allen P. M., Greenberg P. D. and Kranz D. M. (2009) Structural features of T cell receptor variable regions that enhance domain stability and enable expression as single-chain ValphaVbeta fragments. Mol Immunol 46, 902-16.
53. Richman S. A. and Kranz D. M. (2007) Display, engineering, and applications of antigen-specific T cell receptors. Biomol Eng 24, 361-73.
54. Rock K. L. and Goldberg A. L. (1999) Degradation of cell proteins and the generation of MHC class I-presented peptides. Annu Rev Immunol 17, 739-79.
55. Rudolph M. G., Stanfield R. L. and Wilson I. A. (2006) How TCRs bind MHCs, peptides, and coreceptors. Annu Rev Immunol 24, 419-66.

56. Sadelain M., Brentjens R. and Riviere I. (2009) The promise and potential pitfalls of chimeric antigen receptors. Curr Opin Immunol 21, 215-23.
57. Sami M., Rizkallah P. J., Dunn S., Molloy P., Moysey R., Vuidepot A., Baston E., Todorov P., Li Y., Gao F., Boulter J. M. and Jakobsen B. K. (2007) Crystal structures of high affinity human T-cell receptors bound to peptide major histocompatibility complex reveal native diagonal binding geometry. Protein Eng Des Sel 20, 397-403.
58. Schrama D., Reisfeld R. A. and Becker J. C. (2006) Antibody targeted drugs as cancer therapeutics. Nat Rev Drug Discov 5, 147-59.
59. Scott J. K. and Smith G. P. (1990) Searching for peptide ligands with an epitope library. Science 249, 386-90.
60. Skowera A., Ellis R. J., Varela-Calvino R., Arif S., Huang G. C., Van-Krinks C., Zaremba A., Rackham C., Allen J. S., Tree T. I., Zhao M., Dayan C. M., Sewell A. K., Unger W. W., Drijfhout J. W., Ossendorp F., Roep B. O. and Peakman M. (2008) CTLs are targeted to kill beta cells in patients with type 1 diabetes through recognition of a glucose-regulated preproinsulin epitope. J Clin Invest 118, 3390-402.
61. Smith C. A. and Kortemme T. (2008) Backrub-like backbone simulation recapitulates natural protein conformational variability and improves mutant side-chain prediction. J Mol Biol 380, 742-56.
62. Soo Hoo W. F., Lacy M. J., Denzin L. K., Voss E. W. J., Hardman K. D. and Kranz D. M. (1992) Characterization of a single-chain T cell receptor expressed in *E. Coli*. Proc. Natl. Acad. Sci. 89, 4759-4763.
63. Starr T. K., Jameson S. C. and Hogquist K. A. (2003) Positive and negative selection of T cells. Annu Rev Immunol 21, 139-76.
64. Starwalt S. E., Masteller E. L., Bluestone J. A. and Kranz D. M. (2003) Directed evolution of a single-chain class II MHC product by yeast display. Protein Eng 16, 147-56.
65. Stone J. D., Chervin A. S., Aggen D. H. and Kranz D. M. (2012) T cell receptor engineering. Methods Enzymol 503, 189-222.
66. Stone J. D., Yin Y., Mo M., Weber K. S., Donermeyer D. L., Allen P. M., Mariuzza R. A. and Kranz D. M. (2012) Engineering High-Affinity T Cell Receptor/Cytokine Fusions for Therapeutic Targeting. In Protein Engineering (Edited by Kaumaya P.). InTech.
67. Stroncek D. F., Berger C., Cheever M. A., Childs R. W., Dudley M. E., Flynn P., Gattinoni L., Heath J. R., Kalos M., Marincola F. M., Miller J. S., Mostoslaysky G., Powell D. J., Jr., Rao M., Restifo N. P., Rosenberg S. A., O'Shea J. and Melief C. J. (2012) New directions in cellular therapy of cancer: a summary of the summit on cellular therapy for cancer. J Transl Med 10, 48.
68. Swers J. S., Kellogg B. A. and Wittrup K. D. (2004) Shuffled antibody libraries created by in vivo homologous recombination and yeast surface display. Nucleic Acids Res 32, e36.
69. Tayal V. and Kalra B. S. (2008) Cytokines and anti-cytokines as therapeutics—an update. Eur J Pharmacol 579, 1-12.
70. Thakur A. and Lum L. G. (2010) Cancer therapy with bispecific antibodies: Clinical experience. Curr Opin Mol Ther 12, 340-9.
71. Tonegawa S. (1988) Nobel lecture in physiology or medicine—1987. Somatic generation of immune diversity. In Vitro Cell Dev Biol 24, 253-65.
72. Tsomides T. J., Aldovini A., Johnson R. P., Walker B. D., Young R. A. and Eisen H. N. (1994) Naturally processed viral peptides recognized by cytotoxic T lymphocytes on cells chronically infected by human immunodeficiency virus type 1. J Exp Med 180, 1283-93.
73. Turner D. J., Ritter M. A. and George A. J. (1997) Importance of the linker in expression of single-chain Fv antibody fragments: optimisation of peptide sequence using phage display technology. J Immunol Methods 205, 43-54.
74. Utz U., Banks D., Jacobson S. and Biddison W. E. (1996) Analysis of the T-cell receptor repertoire of human T-cell leukemia virus type 1 (HTLV-1) Tax-specific CD8+ cytotoxic T lymphocytes from patients with HTLV-1-associated disease: evidence for oligoclonal expansion. J Virol 70, 843-51.
75. Varela-Rohena A., Molloy P. E., Dunn S. M., Li Y., Suhoski M. M., Carroll R. G., Milicic A., Mahon T., Sutton D. H., Laugel B., Moysey R., Cameron B. J., Vuidepot A., Purbhoo M. A., Cole D. K., Phillips R. E., June C. H., Jakobsen B. K., Sewell A. K. and Riley J. L. (2008) Control of HIV-1 immune escape by CD8 T cells expressing enhanced T-cell receptor. Nat Med 14, 1390-5.
76. Weber K. S., Donermeyer D. L., Allen P. M. and Kranz D. M. (2005) Class II-restricted T cell receptor engineered in vitro for higher affinity retains peptide specificity and function. Proc Natl Acad Sci USA 102, 19033-8.
77. Wong R. L., Liu B., Zhu X., You L., Kong L., Han K. P., Lee H. I., Chavaillaz P. A., Jin M., Wang Y., Rhode P. R. and Wong H. C. (2011) Interleukin-15:Interleukin-15 receptor alpha scaffold for creation of multivalent targeted immune molecules. Protein Eng Des Sel 24, 373-83.

U.S. Patents

U.S. Pat. No. 7,569,357; Filed Feb. 20, 2004; Issued Aug. 4, 2009; Board of Trustees University of Illinois. High affinity TCR proteins and methods.
U.S. Pat. No. 7,465,787; Filed Dec. 16, 2003; Issued Dec. 16, 2008; Board of Trustees University of Illinois. Yeast cell surface display of proteins and uses thereof.
U.S. Pat. No. 6,759,243; Filed Dec. 6, 2000; Issued Jul. 6, 2004; Board of Trustees University of Illinois. High affinity TCR proteins and methods.
U.S. Pat. No. 6,699,658; Filed Jan. 20, 1998; Issued Mar. 2, 2004; Board of Trustees University of Illinois. Yeast cell surface display of proteins and uses thereof.
U.S. Pat. No. 6,696,251; Filed Nov. 28, 2000; Issued Feb. 24, 2004; Board of Trustees University of Illinois. Yeast cell surface display of proteins and uses thereof.
U.S. Pat. No. 6,423,538; Filed Nov. 28, 2000; Issued Jul. 23, 2002; Board of Trustees University of Illinois. Yeast cell surface display of proteins and uses thereof.
U.S. Pat. No. 6,300,065; Filed Aug. 26, 1998; Issued Oct. 9, 2001; Board of Trustees University of Illinois. Yeast cell surface display of proteins and uses thereof.
U.S. Pat. No. 8,143,376; Filed May 18, 2005; Issued Mar. 27, 2012; Immunocore Limited; High affinity NY-ESO T cell receptor.
U.S. Pat. No. 8,088,379; Filed Sep. 26, 2007; Issued Jan. 2, 2012; Immunocore Limited; Modified T cell receptors and related materials and methods.
U.S. Pat. No. 8,017,730; Filed May 19, 2006; Issued Sep. 6, 2011; Immunocore Limited; T cell receptors which bind to VYGFVRACL-HLA-A24.
U.S. Pat. No. 7,763,718; Filed Oct. 29, 2007; Issued Jul. 27, 2010; Immunocore Limited; Soluble T cell receptors.
U.S. Pat. No. 7,666,604; Filed Jul. 9, 2003; Issued Feb. 23, 2010; Immunocore Limited; Modified soluble T cell receptor.

U.S. Pat. No. 7,608,410; Filed Oct. 7, 2008; Issued Oct. 27, 2009; Immunocore Limited; Method of improving T cell receptors.

U.S. Pat. No. 7,569,664; Filed Oct. 3, 2003; Issued Aug. 4, 2009; Immunocore Limited; Single chain recombinant T cell receptors.

U.S. Pat. No. 8,105,830; Filed Nov. 5, 2002; Issued Jan. 31, 2012; Altor Bioscience Corporation; Polyspecific binding molecules and uses thereof.

U.S. Pat. No. 6,534,633; Filed Oct. 22, 1999; Mar. 18, 2003; Altor Bioscience Corporation; Polyspecific binding molecules and uses thereof.

---

What is claimed is:

1. A modified T cell receptor, or antigen-binding fragment thereof, comprising a Vα and a Vβ derived from a T cell clone, wherein the T cell receptor binds to a complex of the peptide WT1 and the HLA-A2 molecule, wherein the T cell receptor comprises the Vβ amino acid sequence set forth in SEQ ID NO:1 and the Vα amino acid sequence set forth in SEQ ID NO:2.

2. A host cell that expresses the T cell receptor of claim 1.

3. The host cell of claim 2, wherein the cell is a human T cell.

4. A modified T cell receptor, or antigen-binding fragment thereof, comprising a Vα and a Vβ derived from a wild type T cell receptor, wherein the Vα and Vβ, respectively, comprise the amino acid sequence set forth in SEQ ID NOS:2 and 3; SEQ ID NOS: 4 and 3; SEQ ID NOS: 4 and 21; or SEQ ID NOS:22 and 21.

5. The modified T cell receptor of claim 4, wherein the modified T cell receptor comprises the Vβ amino acid sequence set forth in SEQ ID NO:3 and the Vα amino acid sequence set forth in SEQ ID NO:4.

6. The modified T cell receptor of claim 4, wherein the modified T cell receptor comprises the single-chain T cell receptor with the amino acid sequence set forth in SEQ ID NO:5.

7. The modified T cell receptor of claim 4, comprising the Vα amino acid sequence set forth in SEQ ID NO:2 and the Vβ amino acid sequence set forth in SEQ ID NO:3.

8. A modified T cell receptor of claim 4 that binds to a complex of the peptide WT1 and the HLA-A2 molecule with a nanomolar or higher affinity, wherein the modified T cell receptor binds the complex with a $K_D$ value less than or equal to $10^{-6}$M.

9. A modified T cell receptor of claim 4 that is in soluble form.

10. A therapeutic agent that targets cancer cells that express the WT1 antigen, wherein the therapeutic agent comprises the modified T cell receptor of claim 8.

11. A therapeutic agent that targets cancer cells that express the WT1 antigen, wherein the therapeutic agent comprises a human T cell that expresses the modified T cell receptor of claim 4.

12. A method of treating a subject having a cancer that expresses the WT1 antigen comprising administering the therapeutic agent of claim 10.

13. A method of treating a subject having a cancer that expresses the WT1 antigen comprising administering the therapeutic agent of claim 11.

* * * * *